United States Patent [19]
Claremon

[11] Patent Number: 4,579,851
[45] Date of Patent: Apr. 1, 1986

[54] SUBSTITUTED AND BRIDGED TETRAHYDROPYRIDINES USEFUL AS CALCIUM ENTRY BLOCKERS

[75] Inventor: David A. Claremon, Audubon, Pa.

[73] Assignee: Merck & Co., Inc., Rahway, N.J.

[21] Appl. No.: 614,885

[22] Filed: May 29, 1984

[51] Int. Cl.$^4$ ................. A61K 31/455; C07D 491/08; C07D 495/08
[52] U.S. Cl. ..................................... 514/291; 546/80; 546/89; 546/92
[58] Field of Search ............................ 546/80, 89, 92; 424/256; 514/291

[56] References Cited

PUBLICATIONS

Hof, R. P. "Calcium Antagonist and the Peripheral Circulation:" Br. J. Pharmac., 78, 375-394 (1983).
Hof, R. P. "The Calcium Antagonists PY 108-068 and Verapanil Diminish the Effects of Angiotensin II:" Br. J. Pharmac., 82, 051-060 (1984).
Van Meel, J. C. A., et al. "The Inhibitory Effect of Newer Calcium Antagonists" Arch. Int. Pharmacodyn, 260, 206-217 (1982).
Schramm, M. "Novel Dihydropyridines with Positive Inotropic Action" Nature vol. 303 Jun. 9, 1983 pp. 535-537.
Bossert, F. et al. "4-14 Aryldihydropyridines" Angew. Chem. Ed. Engl. 20, pp. 762-769 (1981).

Primary Examiner—Henry R. Jiles
Assistant Examiner—Dale A. Bjorkman
Attorney, Agent, or Firm—Salvatore C. Mitri; Michael C. Sudo

[57] ABSTRACT

Substituted dihydropyridines and substituted and bridged tetrahydropyridines are disclosed which are useful as calcium entry blockers.

10 Claims, No Drawings

SUBSTITUTED AND BRIDGED TETRAHYDROPYRIDINES USEFUL AS CALCIUM ENTRY BLOCKERS

BACKGROUND OF THE INVENTION

Substituted dihydropyridines are known to be useful for reducing blood pressure, effecting dilation of the coronary vessels, and preventing vasospasms. Typical of such substituted dihydropyridines are those disclosed in U.S. Pat. Nos. 3,923,818; 3,905,970; 4,044,141; 4,237,137; and, 4,285,955. The substituted dihydropyridines disclosed in these patents do not include bridged ring structures.

Weller et al. [*J. Org. Chem,* 48, 3061-67 (1983)] disclose fused ring and bridged ring structures (e.g., spiro piperidines, spiro pyridines) but indicate that in such structures no exceptionally active analgesics have been found. Furthermore, the bridge portion in these structures is from the ortho position of the benzene ring to the para position of the piperidine or pyridine rings.

SUMMARY OF THE INVENTION

This invention relates to novel substituted and bridged pyridines and related compounds which are useful as calcium channel blockers and to methods for preparing such compounds. The compounds of this invention can be represented by the general formula:

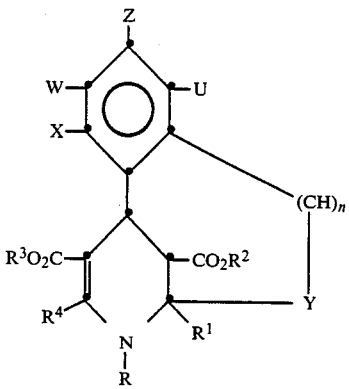

1 wherein:
R is hydrogen; $C_1$-$C_8$ straight chain or branched alkyl; benzyl;
$R^1$ and $R^4$ are independently hydrogen; straight chain or branched, saturated or unsaturated hydrocarbon having up to 8 carbon atoms; hydroxy-$C_1$-$C_8$-alkyl; $CO_2$-loweralkyl of $C_1$-$C_8$ $C_3$-$C_8$ cycloalkyl;
$R^2$ and $R^3$ are independently straight chain or branched, saturated or unsaturated hydrocarbon having up to 8 carbon atoms; $C_3$-$C_8$ cycloalkyl; $C_2$-$C_8$ alkyl interrupted by 1 to 2 oxygen atoms or substituted with $NR^5R^6$ wherein $R^5$ and $R^6$ can independently be hydrogen, $C_1$-$C_8$ alkyl, or aralkyl wherein the alkyl group has up to 8 carbon atoms and the aryl has 6 carbon atoms, or $R^5$ and $R^6$ together with the N atom can be joined to form a 5- or 6-membered ring wherein the 6-membered ring can contain an O, S, or N heteroatom and the N heteroatom can be substituted with $C_1$-$C_6$alkyl;
X, W, Z and U can independently be hydrogen; phenyl and substituted phenyl wherein the substituents can be 1-2 halo (Cl, Br, F) atoms; halo; $NO_2$; trifluoromethyl; $C_1$-$C_8$alkoxy; $C_1$-$C_8$ linear or branched alkyl, alkenyl or alkynyl; $C_1$-$C_8$ thioalkyl wherein the S atom can be substituted with 1-2 O atoms; cyano; $NH_2$;

wherein $R^7$ is $C_{1-8}$ alkoxy or $C_1$-$C_8$ alkyl; provided that two of X, W, Z and U are hydrogen; or X and W, W and Z, or Z and U, together with the phenyl ring, form naphthyl or benzooxadiazole rings;
Y is O; S; SO;
n is 0 or 1;
and, the pharmaceutically acceptable acid addition salts thereof.

Preferred are compounds of Formula 1 wherein:
r is hydrogen;
$R^1$ and $R^4$ are independently $C_{1-8}$ alkyl;
$R^2$ and $R^3$ are independently $C_{1-8}$ alkyl which can be substituted with $NR^5R^6$ wherein $R^5$ and $R^6$ are as defined above;
X is hydrogen or halo;
U and W can each be $NO_2$; $CF_3$; or halo;
Z is hydrogen;
Y is O or S; and,
n is 0 or 1.

Most preferred are those compounds of Formula 1 wherein:
R is hydrogen;
$R^1$ and $R^4$ are methyl;
$R^2$ and $R^3$ are $C_{1-4}$ alkyl;
X is hydrogen or halo;
U and W can each be $NO_2$, $CF_3$ or halo;
Z is hydrogen;
Y is O or S; and,
n is 0 or 1.

The compounds of the invention can be prepared by the methods set forth hereinbelow. In these methods, unless otherwise indicated, the starting materials employed are commercially available or known in the literature, R–$R^4$, W, X, Y, Z, U, and n are as defined above, and all temperatures are in degrees Celsius.

REACTION SCHEME I

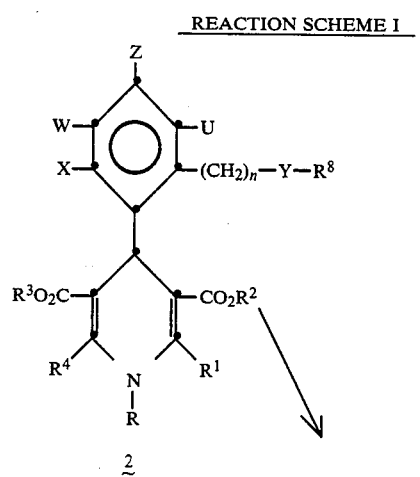

2

-continued
REACTION SCHEME I

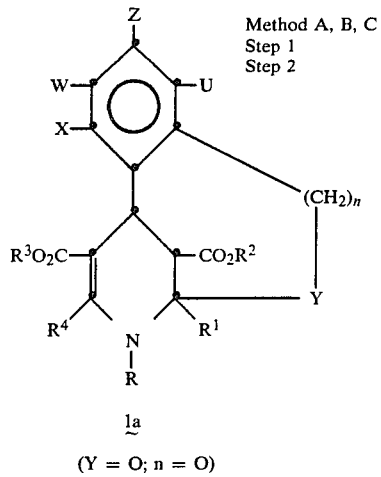

1a (Y = O; n = O)

METHOD A

Step 1

As shown in Reaction Scheme I, either dihydropyridine 2 ($R^8 = C_1-C_8$ alkyl, benzyl, paramethoxy benzyl; X, W, Z and U are not alkoxy, Y is O, and n is o) or W and X, W and Z, or Z and U with the phenyl form naphthyl [both of which compounds can be prepared as described in U.S. Pat. No. 3,959,296] is treated with about 1–5 mole equivalent (meq) (preferably 1 meq) of a boron halide or boron halide complex such as boron tribromide, ($BBr_3$), boron trichloride, ($BCl_3$), boron tribromide/dimethylsulfide ($BBr_3/DMS$), dimethylboron bromide or pyridine/hydrochloride or aluminum chloride ($AlCl_3$) (preferably $BBr_3$) neat or in a suitable solvent such as methylene chloride ($CH_2Cl_2$), chloroform ($CH_2Cl_3$), benzene (preferably ($CH_2Cl_2$)) at a temperature of about $-78°$ to the reflux temperature of the solvent (preferably 25° C. to reflux) under an inert atmosphere (Ar or $N_2$) for a period of about 1–25 hours (preferably 1 hour). The intermediate lactone compound 3 (Reaction Scheme II, Method D) is isolated and treated as described below in Step 2.

Step 2

The reaction mixture, maintained under the inert atmosphere, is then treated with about 2–5 meq (preferably 5 meq) potassium carbonate, potassium hydride, lithium hydride, or sodium hydride (preferably potassium carbonate) and 2–25 meq of $R^2OH$, preferably about 10 meq, neat or in a suitable solvent such as dimethylformamide (DMF), dimethoxyethane (DME) or tetrahydrofuran (THF) at about 25°–125° C. (preferably about 25° C.) for about 1–48 hours to afford a compound 1a of Formula 1.

METHOD B

Step 1

In this method ($R^8 = CH_2-C_6H_5$, Y=O, n=0, 1), compound 2 (Reaction Scheme I) is treated with hydrogen under pressure (1 atm. or 2–3 atm.) in the presence of about 10%–100% weight equivalents of a catalyst such as 5% Pd/C, 10% Pd/C or $PtO_2$ in a suitable solvent such as ethanol (EtOH), ethyl acetate, methanol ($CH_3OH$), isopropanol, petroleum ether, preferably EtOH, at 10°–40° C. (preferably 25° C.) for about 25–36 hours to obtain compound 1a.

Step 2

Compound 2 is first treated as described above in Method B, Step 1, to obtain an intermediate phenol dihydropyridine which is then treated with about 0.1–0.3 meq (preferably 0.1 meq) of an acid (toluenesulfonic acid, camphorsulfonic acid, trifluoroacetic acid, methanesulfonic acid, sulfuric acid; preferably, camphorsulfonic acid) in a solvent such as $CH_2Cl_2$, $CHCl_3$, dichloroethane, THF, DME, or mixtures thereof (preferably methylene chloride) at about 25° to 50° C. for about 2–24 hours to obtain compound 1a.

METHOD C

Dihydropyridine 2 ($R^8 = CH_2-C_6H_5$ or

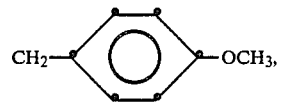

Y=O or S, n=0 or 1) (Reaction Scheme I) is treated under an inert atmosphere (Ar or $N_2$) with about 5–50 meq (preferably 10 meq) trifluoroacetic acid neat or in the presence of a solvent (anisole, $CH_2Cl_2$, $CHCl_3$, dichloroethane) at 25°–100° C. (preferably 25° C.) for about 10–60 minutes to obtain the Formula 1 compound.

REACTION SCHEME II, Method D

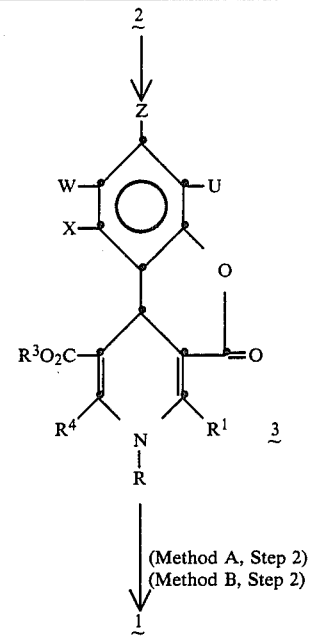

(Method A, Step 2)
(Method B, Step 2)

1

METHOD D

In this method (Reaction Scheme II $R^8 = C_1-C_8$alkyl, benzyl, paramethoxybenzyl; Y=O; n=O; and, X, W, Z and U are not alkoxy), dihydropyridine or naphthyldihydropyridine 2 is treated under an inert atmosphere (Ar or $N_2$) with about 1 meq $BBr_3$ or $BCl_3$ in an organic solvent ($CH_2Cl_2$, dichloromethane, $CHCl_3$, benzene; preferably $CH_2Cl_2$) at a temperature of about $-78°$ to 40° C. for about 3 hours to obtain oxo-carbonyl bridged dihydropyridine intermediate 3. This intermediate 3 is then isolated and treated as described above in Method A, Step 2, to obtain the phenol dihydropyridine intermediate (Method B, Step 2) which is treated as described above in Method B, Step 2, to afford compound 1a.

REACTION SCHEME III, METHOD E

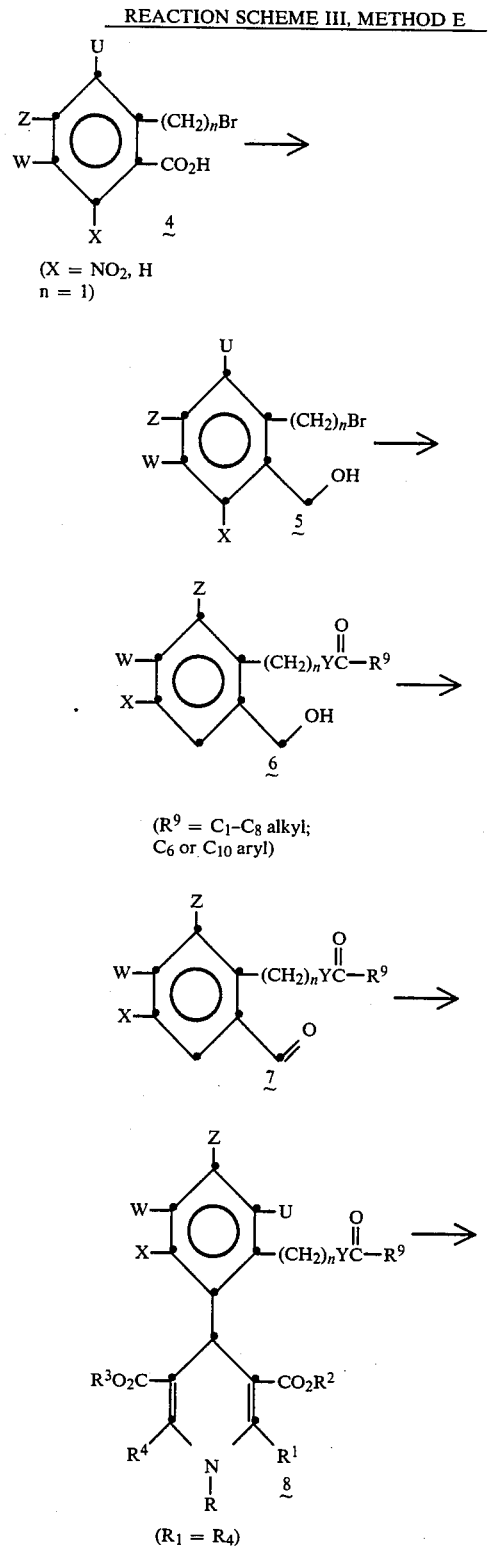

-continued
REACTION SCHEME III, METHOD E

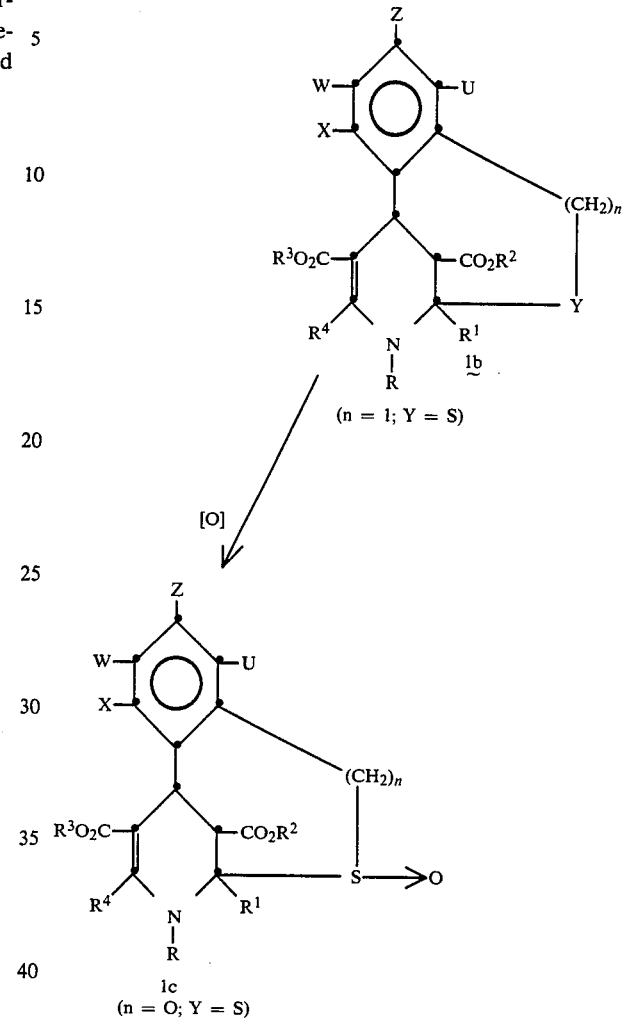

METHOD E

Step 1

As shown in Reaction Scheme III, substituted benzoic acid 4 is treated under an inert atmosphere (Ar, $N_2$) with about 1 meq of a borane complex such as borane/THF, borane/DMS, borane/piperidine (preferably borane/THF) in a polar aprotic solvent (THF, $CH_2Cl_2$, toluene; preferably THF) at about 0°–85° (preferably 25° C.) for 2 hours to obtain methoxy benzoic acid intermediate 5.

Step 2

Intermediate 5 is then treated with about 1.2 meq of a thioalkanoate compound, preferably potassium thioacetate

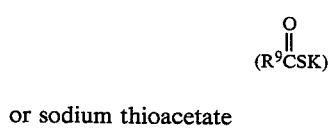

or sodium thioacetate

($R^6 = C_1$–$C_8$ alkyl; $C_6$ or $C_{10}$ aryl) using DMF as the solvent under the same conditions as in Step 1 to yield the methylthioacetate intermediate 6.

Step 3

Thioacetate intermediate 6 is then reacted with about 2 meq (preferably 1.5 meq) $MnO_2$, pyridinium chlorochromate (PCC), Collins reagent, dimethylsulfoxide (DMSO), oxalylchoride/triethylamine (TEA) (preferably $MnO_2$) in an organic solvent ($CH_2Cl_2$, dichloroethane, benzene, hexane; preferably $CH_2Cl_2$) at about $-75°$ to $110°$ C. (preferably $25°$ C.) for about 48 hours to obtain aldehyde intermediate 7.

Step 4

Aldehyde intermediate 7 is reacted under an inert atmosphere (Ar, $N_2$) with about 1 meq each of acetoacetate

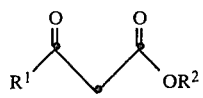

and aminocrotonate

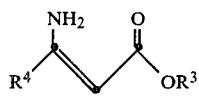

in a polar solvent (isopropanol, EtOH, $CH_3OH$, toluene, DME, THF; preferably isopropanol) at $60°$–$130°$ C., preferably the reflux temperature of the solvent to afford dihydropyridine intermediate 8.

Step 5

Upon treatment with a base ($K_2CO_3$, KOH, $Na_2CO_3$, NaOH; preferably $K_2CO_3$) in a lower alkanol solvent (methanol, ethanol; preferably methanol) under an inert atmosphere (Ar, $N_2$) at a temperature of about $25°$–$110°$ C. (preferably $25°$ C.) for 2 hours, intermediate 8 is converted to the methyl-sulfur bridged compound 1b of the invention.

Further treatment of compound 1b with a suitable oxidizing agent such as metachloroperoxybenzoic acid, osmium tetroxide, sodium periodate, hydrogen peroxide, t-butyl hydroperoxide, and the like, affords the sulfoxide compound 1c of the invention.

REACTION SCHEME IV, METHOD F

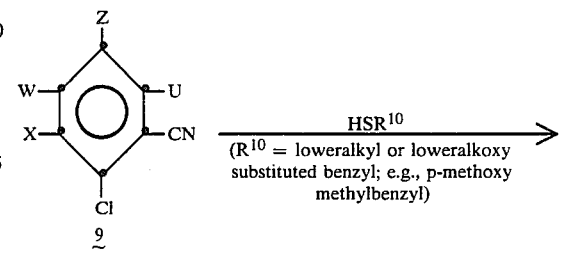

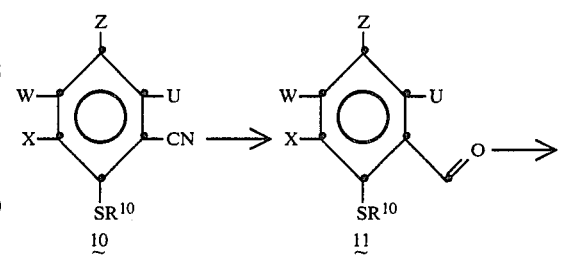

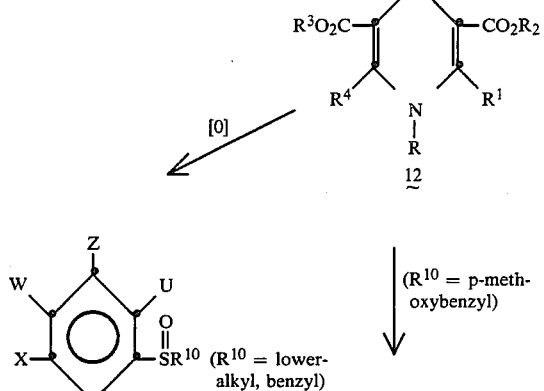

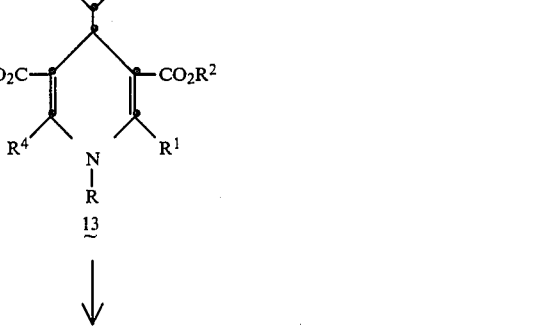

-continued
REACTION SCHEME IV, METHOD F

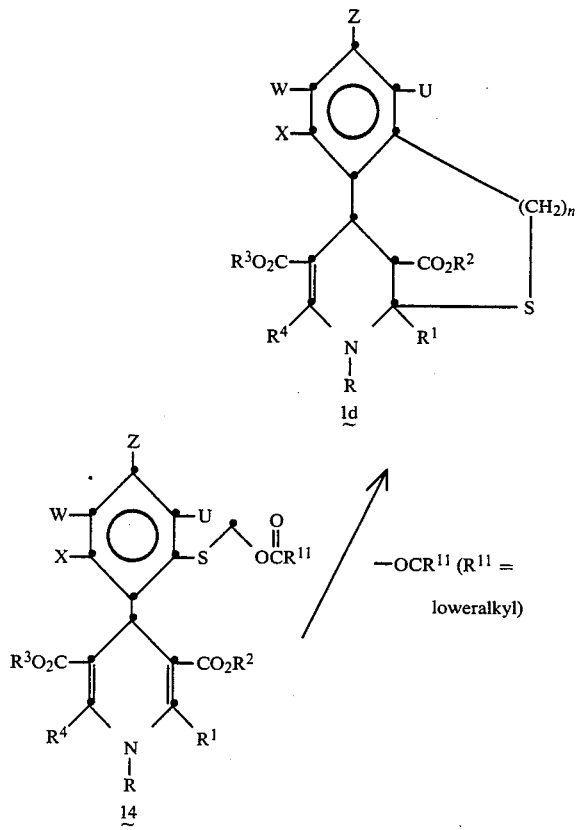

METHOD F

As shown in Reaction Scheme IV, substituted halobenzonitrile 9 is treated with the sulfhydryl compound, $HSR^{10}$ (1-5 meq) in a solvent (dimethylformamide (DMF), $CH_3OH$, EtOH, isopropanol or N-methyl-2-pyrolidinone) in the presence of an alkali (lithium hydride, sodium hydride, potassium hydride, potassium carbonate, sodium methoxide, sodium ethoxide, potassium hydroxide) at about 0°-100° C. (preferably 0°-25° C.) for about 5 hours to obtain substituted thiobenzonitrile intermediate 10.

Treatment of intermediate 10 with diisobutylaluminum hydride (DIBAL) (1-2 meq) under an inert atmosphere (Ar, $N_2$) in an organic solvent ($CH_2Cl_2$, THF, hexane, toluene, dichloroethane) at about −78° C. to the reflux temperature of the solvent (preferably −78° to 25° C.) for about 3 hours followed by treatment with an aqueous acid (HCl, $H_2SO_4$, acetic acid) affords aldehyde intermediate 11.

Intermediate 11 is then reacted with 1 meq each of an acetoacetate and an aminocrotonate in the same solvent at a temperature of about 25°-130° C. for about 12 hours to obtain dihydropyridine intermediate 12 which can then be reacted with trifluoroacetic acid and anisole (each at 5-50 meq; preferably 5 meq) either neat or in an organic solvent ($CH_2Cl_2$, dichloroethane, or $CHCl_3$), under an inert atmosphere (Ar, $N_2$) at about 0°-100° C. (preferably 0°-25° C.) for about 15 minutes to directly yield the sulfur bridged compound 1d of the invention.

Alternatively, dihydropyridine intermediate 12 is oxidized as described in Method E, Step 5, to obtain sulfonyl dihydropyridine intermediate 13 which is then treated with an alkanoic acid anhydride such as acetic anhydride

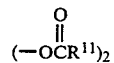

ps (10-100 meq, preferably 5-50 meq) under an inert atmosphere (Ar, $N_2$) at about 80°-130° C. (preferably 90° C.) for about 1 hour to obtain dihydropyridine intermediate 14. Upon treatment with an alkali (potassium carbonate, sodium hydride, lithium hydride, potassium hydride, potassium hydroxide, sodium hydroxide) under an inert atmosphere (Ar, $N_2$) in a lower alkanol organic solvent (ethanol, methanol) at about 25°-100° C. (preferably 25° C.) for about 5 hours, intermediate 14 affords compound 1d.

Compounds of Formula 1 can exist in different isomeric forms such as, for example, threo, erythro, diasteromeric, enantiomeric, and all such forms are included within the scope of this invention.

As indicated above, the compounds of this invention are useful as calcium entry blockers, and thus have broad pharmacological utility in that they exhibit (i) pronounced and long-lasting vasodilating effect accompanied by an energy-sparing effect on cardiac metabolism; (ii) antiarrythmic and antianginal action on cardiac muscle; (iii) vascular spasmolytic action; (iv) antihypertensive action; (v) spasmolytic action on the smooth muscle of the gastrointestinal and urogenital tracts and the cerebrovascular and respiratory system; (vi) are useful cholesterolemic and lipademic agents and for treating cerebral and peripheral circulatory disorders; (vii) protect ischemic myocardium; (viii) inhibit irritable bowel syndrome and esophagus spasm; and, (ix) inhibit migraine. Some of these compounds may also be useful cardiotonic agents.

The compounds of the present invention were found to inhibit vascular calcium contraction, reduce cardiac contractile force, inhibit tracheal calcium contraction, inhibit calcium uptake in pituitary cells, and displace tritiated nitrendepine from membranes.

The compounds of the present invention can be administered in any suitable form; e.g. orally, sublingually, transdermally, or parenterally; i.e. intravenously, interperitoneally, etc. Thus, the compounds can be offered in a form (a) for oral administration e.q. as tablets in combination with other compounding ingredients customarily ued such as talc, vegetable oils, polyols, benzyl alcohols, gums, gelatin, starches and other carriers; dissolved or dispersed or emulsified in a suitable liquid carrier; in capsules or encapsulated in a suitable encapsulating material; or (b) for sublingual administration; e.g., nitroglycerine tablets, lactose tablets, and the like, for rapid dissolution or high molecular weight methylcellulose tablets, carboxymethylcellulose tablets, and the like, for slower, time-releasing delivery; or, (c) for parenteral administration e.g. dissolved or dispersed in a suitable liquid carrier or emulsified. The ratio of active compound to compounding ingredients i.e. carrier, diluent etc. will vary as the dosage form requires. Whatever form is used, the amount of compound of the present invention administered should be sufficient to achieve the pharmaceutical and/or therapeutic effect desired or required in the patient. Generally, doses of the compounds of the invention of from about 30 to about 3000 mg per day may be used, preferably about 100 to about 1000 mg per day. Dosages may be single or multiple depending on the daily total required and the unit dosage administered. Of course, the dose will vary depending upon the nature and severity of disease, weight of the patient, and other factors which a person skilled in the art will recognize.

It is often advantageous to administer compounds of this invention in combination with angiotensin converting enzyme inhibitors and/or antihypertensives and/or diuretics and/or B-blocking agents, and/or cardiotonic agents. For example, the compounds of this invention can be given in combination with such compounds as enalapril, hydralazine hydrochloride, hydrochlorothiazide, methyldopa, timolol, digitalis and the like, as well as admixtures and combinations thereof.

Typically, the individual daily dosages for these combinations can range from about one-fifth of the minimally recommended clinical dosages to the maximum recommended levels for the entities when they are given singly. Naturally, these dose ranges can be adjusted on a unit basis as necessary to permit divided daily dosages and, as noted above, can be varied depending on the nature and severity of the disease, weight of patient, special diets and other factors.

DETAILED DESCRIPTION OF THE INVENTION

The following examples are provided to further illustrate the best mode currently known for obtaining the compounds of the invention, but are not to be construed as being limitative of the invention. Unless otherwise indicated, all temperatures are in °C.

EXAMPLE 1

Diethyl 3,6-dihydro-2,4-dimethyl-8-nitro-2,6-methano-2H-1,3-benzoxazocine-5,11-dicarboxylate (18&19)

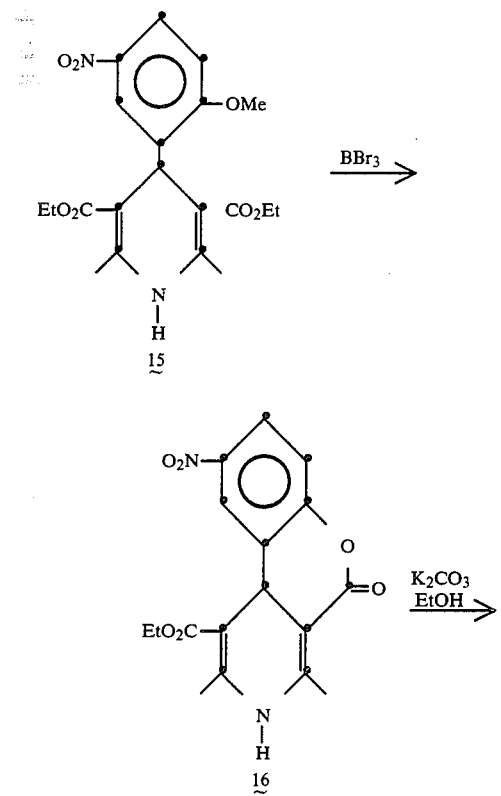

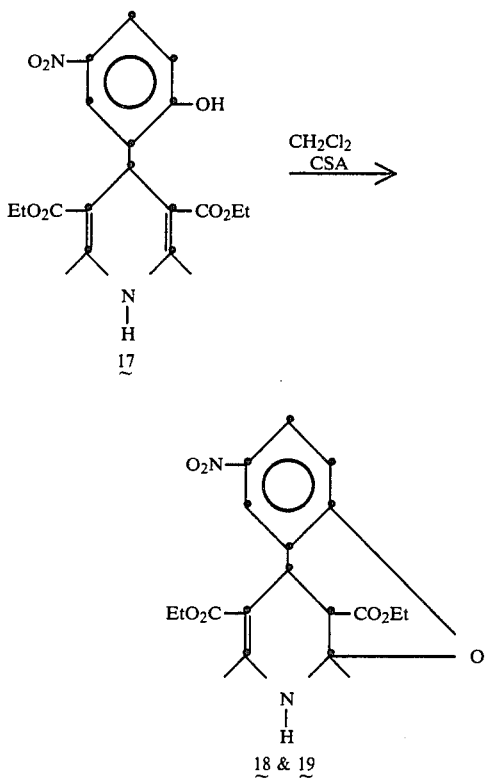

Step 1: Ethyl 3,10-B-dihydro-2,4-dimethyl-9-nitro-5-oxo-5H-(1)-benzopyrano-(3,4-c)pyridine-1-carboxylate A stirred solution of 404 mg (1 mm) of diethyl 2,6-dimethyl-4-(2-methoxy-5-nitrophenyl)-1,4-dihydropyridine-3,5-dicarboxylate 15 in 20 mL of dry $CH_2Cl_2$ cooled to $-78°$ C. under an Ar atmosphere was treated dropwise with 1.25 mL of 1.0M $BBr_3$ in $CH_2Cl_2$. The cooling bath was removed and the mixture was allowed to reach 25° C. After 20 minutes at 25° C., the reaction was quenched with saturated aqueous $NaHCO_3$ and extracted with $CH_2Cl_2$. The combined organic phases were washed with 5% aqueous $NaHCO_3$, and brine, dried (anhydrous $MgSO_4$), filtered, concentrated and recrystallized (5% EtOH in $CH_2Cl_2$) to afford 320 mg (93%) of ethyl 3,10B-dihydro-2,4-dimethyl-9-nitro-5-oxo-5H-(1)-benzopyrano(3,4-c)pyridine-1-carboxylate 16.

$^1$H NMR (360 MHz, DMSO), $\delta = 1.11$ (t, J-7.5 Hz, 3H, $CH_2CH_3$); =2.05, 2.31 (s, 3H each, $CH_3$); 4.04, 4.21 (dq, J=10.5 and 7.5 Hz, 1H each, $OCH_2$); 4.88 (s, 1H, ArC$\underline{H}$); 7.34 (d, J=9.0 Hz, 1H, Ar$\underline{H}$); 7.51 (dd, J-3,10 Hz, $\underline{1H}$, Ar$\underline{H}$); 8.15 (dd, J=3.0, 9.0 $\overline{Hz}$, 1H, Ar$\underline{H}$); 9.19 (bs, 1H, N—$\underline{H}$).

Step 2

A solution of 360 mg (1.05 mm) of pyridine 16 in 30 ml of absolute ethanol under Ar atmosphere was stirred with 1.20 g of powdered anhydrous $K_2CO_3$ at 25° C. for 12 hr. This was neutralized with 30 ml of saturated aqueous $NH_4Cl$ and extracted with $CH_2Cl_2$ (200 ml). The organic portion was washed with pH 7 phosphate buffer (20 mL) and brine, dried (anhydrous $Na_2SO_4$), filtered and concentrated to give 420 mg of crude phenol 17.

Step 3

The crude phenol 17 was dissolved in anhydrous $CH_2Cl_2$ and stirred under Ar with 15 mg of dl-camphorsulfonic acid for 3 hours at 25° C. The mixture was then neutralized by washing with pH 7 phosphate buffer and brine, dried (anhydrous $MgSO_4$), filtered, concentrated to give 400 mg of crude mixture of 2 cyclized products. This was then flash chromatographed (silica gel, 75% ether in hexane) to separate the fast diastereomer 18 (100 mg) and the slower diastereomer. This slower product was further purified by preparative thick layer chromatography (PTLC) (silica gel, 2.5% acetone in $CH_2Cl_2$) and the product crystallized from ether/hexane; yield, 100 mg of 19.

18 $^1$H NMR (360 MHz, $CDCL_3$) $\delta = 1.25$, 1.42 (t, J=7.5 Hz, 3H each, $CH_2CH_3$); $\delta = 1.94$ (s, 3H, $OCCH_3$); $\delta = 2.24$ (s, 3H, $CH_3$); 2.94 (dd, J=2.8, 0.8 Hz, 1H, $CHCO_2$); 4.08–4.36 (bm, 4H, $OCH_2$); 4.67 (d, J=2.8 Hz, 1H, Ar—CH); 5.05 (1H, N—H)); 6.86 (d, J=9.0 Hz, 1H, ArH); 7.98 (dd, J-3.0, 9.0 Hz, 1H, Ar—H); 8.32 (d, J=3.0 Hz, 1H, ArH) m.p. 159°–160° C.

19 $^1$H NMR (360 MHz, $CDCl_3$) $\delta = 1.15$, 1.43 (t, J=7.5 Hz, 3H each, $CH_2CH_3$), 1.89 (s, 3H, $CH_3C$—O), 2.25 (s, 3H, $CH_3$); 2.91 (d, J=2.4 Hz, 1H, $CHCO_2$), 4.09 (dq, J=1.0, 7.5 Hz, 2H, $OCH_2CH_3$), 4.18, 4.34 (dq, J=10.5, 7.5 Hz, 1H each, $OCH_2CH_3$); 4.53 (d, J=2.4 Hz, 1H, ArCH); 4.95 (bs, 1H, NH); 6.87 (d, J=9.0 Hz, 1H, ArH); 7.98 (dd, J=3.0, 9.0 Hz, 1H, ArH); 8.31 (d, J-3.0 Hz, 1H, ArH). m.p. 157°–8° C.

17 $^1$H NMR (360 MHz, $CDCl_3$) $\delta = 1.21$ (t, J=7.5 Hz, 6H, $CH_2CH_3$); 2.42 (s, 6H, $CH_3$); 4.15 (m, $OCH_2$); 5.07 (s, 1H, ArCH); 5.97 (bs, 1H, NH); 6.87 (d, J=9.0 Hz, 1H, ArH); 7.89 (d, J=3.0 Hz, 1H, ArH); 7.98 (dd, J=3.0, 9.0 Hz, 1H, ArH); 9.92 (s, 1H, OH).

EXAMPLE 2

Diethyl 4,5-dihydro-3,5-dimethyl-1,5-methano-1H-naphth(1,2-G)(1,3)oxazocine-2,13-dicarboxylate (21&22)

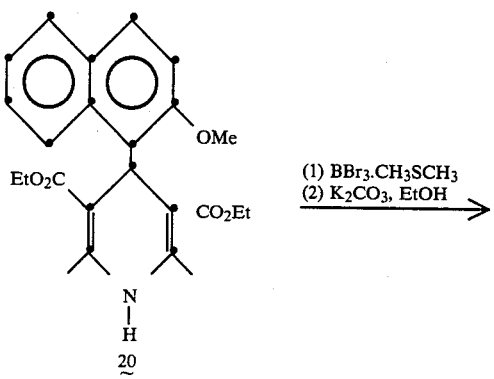

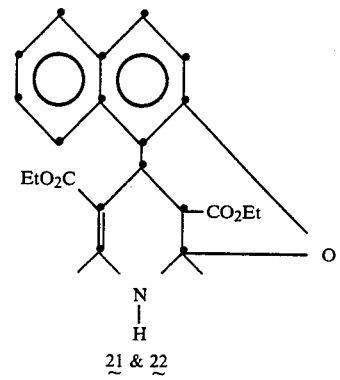

A solution of 2.25 g (5.5 mm) of diethyl 1,4-dihydro-4-(2-methoxy-1-naphthalenyl)-2,6-dimethyl-3,5-pyridinedicarboxylate 20 in 12.0 mL of dry 1,2-dichloroethane was stirred under Ar at 25° C. and treated with 2.40 g (7.68 mm) of $BBr_3.CH_3SCH_3$ complex. After stirring at 25° C. for 20 hours, 10.0 g of anhydrous powdered $K_2CO_3$ and 100 mL of absolute ethanol were added. Stirring was continued for 60 hours at 25°. The reaction was quenched with saturated aqueous $NH_4Cl$ and extracted with 500 ml of $CH_2Cl_2$. The organic layer was washed with pH 7 phosphate buffer and brine, dried (anhydrous $Na_2SO_4$), filtered, evaporated and flash chromatographed (silica gel, 2% acetone in $CH_2Cl_2$).

The separated diastereomers, 21 and 22, were crystallized from ether/hexane; yield: fast (21) 500 mg; slow (22) 100 mg.

21 Fast: $^1$H NMR (360 MHz, $CDCl_3$) $\delta = 1.29$, 1.38 (t, J=7.0 Hz, 3H each, $CH_3CH_2$); 1.96 (s, 3H, $CH_3$—C—O); 2.18 (s, 3H, $CH_3$); 3.06 (dd, J=$H_2O$, 1.0 Hz, 1H, HCCO_2); 4.07–4.33 (m, 4H, $CCH_2CH_3$), 4.97 (bs, 1H, NH); 5.28 (d, J=4.0 Hz, 1H, ArCH); 7.02 (d, J=9.0 Hz, 1H, Ar—H); 7.33 (dt, J=1.0, 7.5 Hz, 1H, ArH); 7.48 (dt, J=1.0, 7.5 Hz, 1H, ArH); 7.61 (d, J=9.0 Hz, 1H, ArH); 7.75 (bd, J=7.5 Hz, 1H, ArH); 8.55 (d, J=9.0 Hz, 1H, ArH).

m.p. 180°–190° C.

22 Slow: $^1$H NMR (300 MHz, $CDCl_3$) $\delta = 1.00$, 1.39 (t, J=7.5 Hz, 3H each, $CH_2CH_3$); 1.94 (s, 3H, $OCCH_3$); 2.36 (s, 3H, $CH_3$); 2.87 (d, J=3.0 Hz, 1H, HCCO_2); 4.00 (q, J=7.5 Hz, 2H, $OCH_2CH_3$); 4.22, 4.32 (dq, J=10.0 Hz, 7.5 Hz, 1H each, $OCH_2CH_3$); 4.91 (bs, 1H, NH); 5.23 (d, J=3.0 Hz, 1H, ArCH); 7.02 (d, J-7.0 Hz, 1H, ArH); 7.31 (bt, J=7.5 Hz, 1H, ArH); 7.46 (bt, J=7.5 Hz, 1H, ArH); 7.59 (d, J=9.0 Hz, 1H, ArH); 7.7 (bd, J=8.0 Hz, 1H, ArH); 8.55 (d, J=9.0 Hz, 1H, ArH);

m.p. 185°–92° C.

EXAMPLE 3

Diethyl 3,6-dihydro-2,4-dimethyl-2,6-methano-2H-1,3-benzoxazocine-5,11-dicarboxylate (26&27)

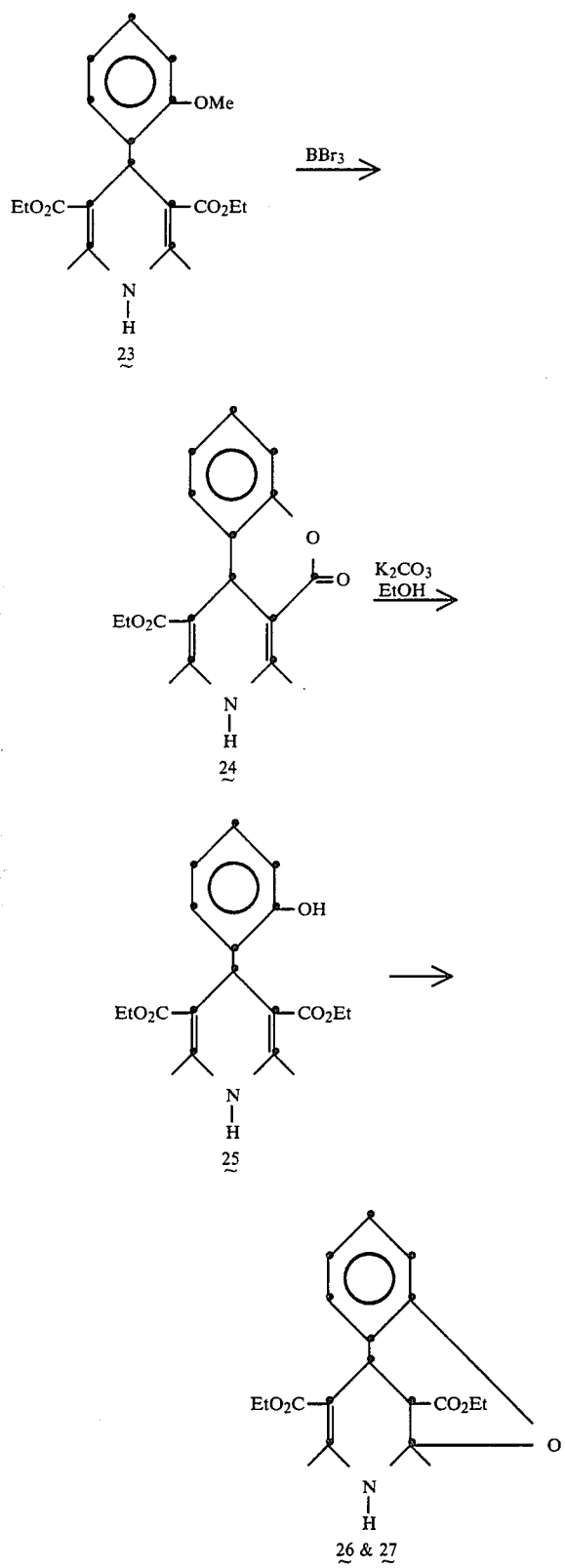

Step 1: Ethyl 3,10B-dihydro-2,4-dimethyl-5-oxo-5H-(1)benzopyrano(3,4-c)pyridine-1-carboxylate (24)

36 mL of BBr$_3$ in CH$_2$Cl$_2$ (1.0M, 36 mm) was added dropwise to a cold (−78° C.) stirred solution of 23, diethyl-1,4-dihydro-4-(2-methoxyphenyl)-2,6-dimethyl-3,5-pyridinedicarboxylate, (10.77 g, 30 mm) in 60 ml of dry CH$_2$Cl$_2$ under an Ar atmosphere. After stirring an additional 15 minutes at −78° C., the reaction mixture was allowed to reach 25° C. and stirred 1 hour. This was quenched with saturated aqueous NH$_4$Cl and extracted with CHCl$_3$. The organic portion was washed with pH 7 phosphate buffer and brine, dried (anhydrous MgSO$_4$), filtered and evaporated to give a solid which was washed with ether and dried 12 hours/40° C./P$_2$O$_5$/1 mm; yield 9.00 g of yellow solid 24 (99%). This was used without further purification in Step 2. Analytical sample was obtained by recrystallization from CH$_2$Cl$_2$.

24 $^1$H NMR (360 MHz, CDCl$_3$) δ=1.95 (t, J=7.5 Hz, 3H, CH$_2$C$\underline{H}_3$); 2.12, 2.34 (s, 3H each, C$\underline{H}_3$); 4.19 (m, 2H, OC$\underline{H}_2$); 4.91 (s, 1H, ArC$\underline{H}$); 5.47 (bs, 1H, N—$\underline{H}$); 6.87 (d, J=7.5 Hz, 1H, Ar$\underline{H}$); 7.07 (t, J=7.5 Hz, 1H, Ar$\underline{H}$); 7.09 (d, J=7.5 Hz, 1H, Ar$\underline{H}$); 7.20 (t, J=7.5 Hz, 1H, ArH).

Ir (KBr)=1690, 1615 cm$^{-1}$.

m.p. 238°–240° C.

Step 2

Lactone 24 (9.00 g) in 150 mL of absolute ethanol was vigorously stirred under Ar with 30 g at powdered anhydrous K$_2$CO$_3$ for 48 hours. This was treated with saturated aqueous NH$_4$Cl and extracted with CH$_2$Cl$_2$. The organic portion as washed with pH 7 phosphate buffer and brine, dried (anhydrous MgSO$_4$), filtered, evaporated and flash chromatographed (silica gel, 60% ether in hexane) to afford 26 and 27.

26 Fast: $^1$H NMR (360 MHz, CDCl$_3$) δ=1.23, 1.34 (t, J=7.5 Hz, 3H each, CH$_2$C$\underline{H}_3$); 1.89 (s, 3H, OCCH$_3$); 2.20 (s, 3H, C$\underline{H}_3$); 2.95 (dd, J=3.0, 1.0 Hz, 1H, C$\underline{H}$CO$_2$); 4.04–4.26 (m, 4H, C$\underline{H}_2$CH$_3$); 4.61 (d, J=3.0 Hz, 1H, ArC$\underline{H}$); 4.97 (bs, 1H, N—$\underline{H}$); 6.79 (d, J=7.5 Hz, 1H, Ar);; 6.84 (dt, J=1.0, 7.5 Hz, 1H, Ar$\underline{H}$); 7.07 (dt, J=1.0, 7.5 Hz, 1H, Ar$\underline{H}$); 7.36 (dd, J=1.6, 7.5 Hz, 1H, ArH).

m.p. 159°–60° C.

27 Slow: $^1$H NMR (360 MHz, CDCl$_3$) δ=1.11, 1.37 (t, J=7.5 Hz, 3H each, CH$_2$C$\underline{H}_3$); 1.87 (s, 3H, OCC$\underline{H}_3$); 2.18 (s, 3H, C$\underline{H}_3$); 2.79 (d, J=3.0 Hz, 1H, $\underline{H}$CCO$_2$); 4.06 (q, J=7.5 Hz, 2H, OCH$_2$); 4.18, 4.25 (dq, J=10.5, 7.5 Hz, 1H each, OC$\underline{H}_3$), 4.50 (d, J=3.0 Hz, 1H, ArC$\underline{H}$); 4.84 (bs, 1H, N$\underline{H}$); 6.79 (d, J=8.0 Hz, 1H, ArH); 6.84 (dt, J=1.0, 8.0 Hz, 1H, ArH); 7.06 (dt, J-10, 8.0 Hz, H, ArH); 7.34 (dd, J=1.0, 8.0 Hz, 1H, Ar$\underline{H}$).

m.p. 100°–102° C.

25 $^1$H NMR (360 MHz, CDCl$_3$) δ=1.19 (t, J=7.5 Hz, 6H, CH$_2$C$\underline{H}_3$); 2.36 (s, 6H, C$\underline{H}_3$); 4.12 (bm, 4H, OC$\underline{H}_2$); 5.09 (s, 1H, ArC$\underline{H}$); 5.78 (bs, 1H, N$\underline{H}$); 6.79 (t, J=7.5 Hz, 1H, Ar$\underline{H}$); 6.88 (d, J=7.5 Hz, 1H, Ar$\underline{H}$); 7.04 (d, J=7.5 Hz, 1H, Ar$\underline{H}$); 7.06 (t, J=8.0 Hz, 1H, Ar$\underline{H}$); 8.72 (s, 1H, O—$\underline{H}$).

m.p. 165°–9° C.

EXAMPLE 4

Diethyl 8,10-dichloro-3,6-dihydro-2,4-dimethyl-2,6-methano-2H-1,3-benzoxazocine-5,11-dicarboxylate (31&32)

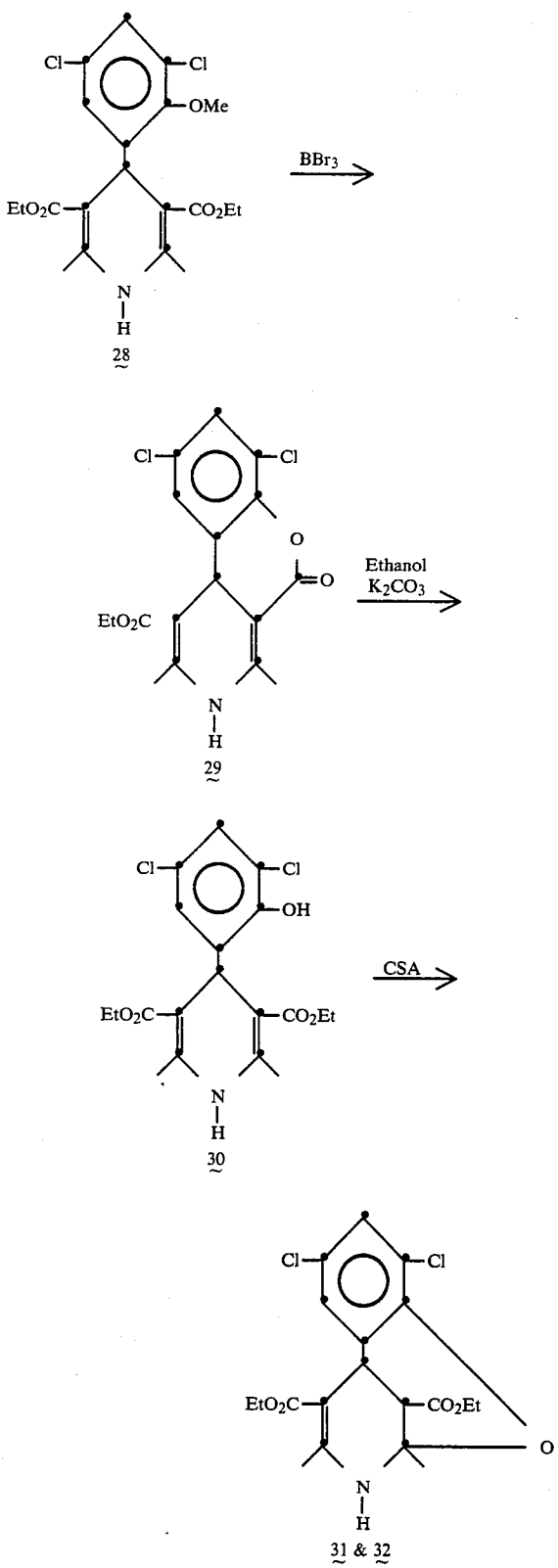

The same procedure was used as in Example 1 to obtain compounds 31 and 32.

Lactone:

29 $^1$H NMR (360 MHz, CDCl$_3$) δ=1.20 (t, J=7.5 Hz, 3H, CH$_2$CH$_3$); 2.14, 2.37 (s, 3H each, CH$_3$); 4.13, 4.27 (dq, J=7.5, 10.0 Hz, 1H each, OCH$_2$); 4.88 (s, 1H, ArCH); 5.83 (bs, 1H, N—N); 6.72, 7.27 (m, 1H each, ArH).

IR (KBr)=1680 cm$^{-1}$

Phenol:

30 $^1$H NMR (360 MHz, CDCl$_3$) δ=1.21 (t, J=7.5 Hz, 6H, CH$_2$CH$_3$); 2.38 (s, 6H, CH$_3$); 4.14 (m, 4H, OCH$_2$); 5.08 (s, 1H, ArCH); 5.81 (bs, 1H, N—H); 6.85 (d, J=3.0 Hz, 1H, Ar—H); 7.16 (d, J=3.0 Hz, 1H, ArH); 9.31 (s, 1H, OH).

m.p. 178°-9° C.

31 Fast: $^1$H NMR (360 MHz, CDCl$_3$/DMSO (3/1)) δ=1.23, 1.34 (t, J=7.5 Hz, 3H each, CH=CH$_3$); 1.94 (s, 3H, OCCH$_3$); 2.21 (s, 3H, CH$_3$); 2.91 (dd, J=3.0, 0.8 Hz, 1H, HCCO$_2$); 4.04-4.28 (m, 4H, OCH$_2$); 4.55 (d, J=3.0 Hz, 1H, ArCH); 7.03 (bs, 1H, N—H); 7.09 (d, J=3.0 Hz, 1H, ArH); 7.25 (d, J=3.0 Hz, 1H, ArH).

m.p. 190°-2° C.

32 Slow: $^1$H NMR (360 MHz, CDCl$_3$ δ=1.15, 1.37 (t, J=7.5 Hz, 3H each, CH$_2$CH$_3$); 1.91 (s, 3H, OCCH$_3$); 2.21 (s, 3H, CH$_3$); 2.83 (d, J=3.0, 1H, HCCO$_2$); 4.09 (q, J=7.5 Hz, 2H, OCH$_2$); 4.17, 4.28 (dq, J-7.5, 11.0 Hz, 1H each, OCH$_2$); 4.46 (d, J=3.0 Hz, 1H, ArCH); 4.96 (bs, 1H, NH); 7.13 (d, J=3.0 Hz, 1H, ArH); 7.26 (d, J=3.0 Hz, 1H, ArH).

m.p. 199°-203° C.

EXAMPLE 5

Diethyl 3,6-dihydro-2,4-dimethyl-2,6-methano-2H-1,3-benzothiazocine-5,11-dicarboxylate (36&37)

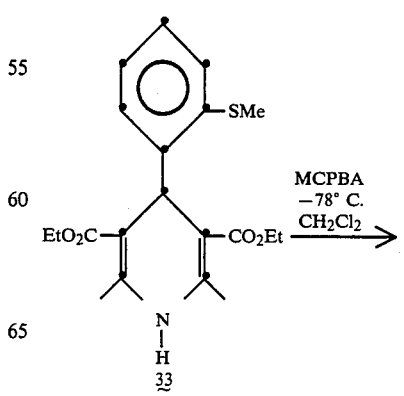

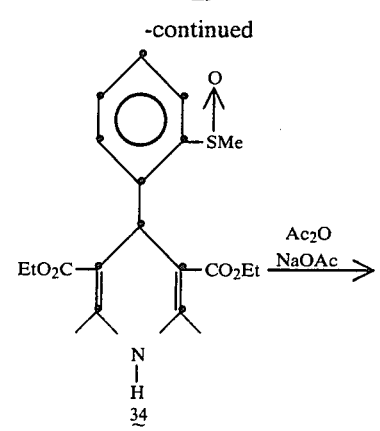

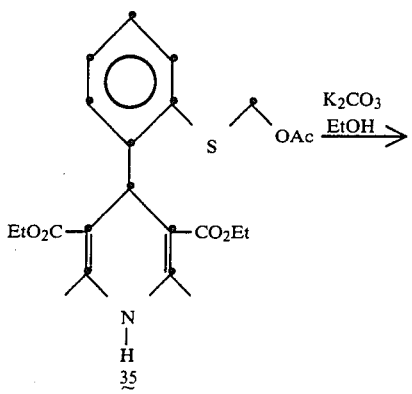

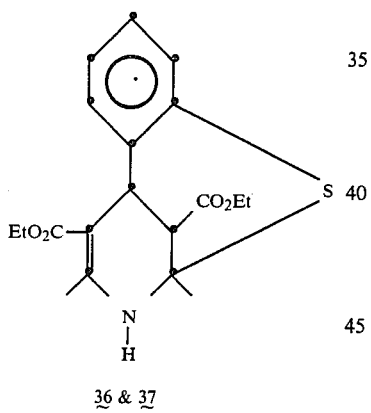

Step 1: Diethyl 1,4-dihydro-2,6-dimethyl-4-[2-(methylsulfinyl)-phenyl]-3,5-pyridinedicarboxylate (34)

A solution of 1.092 g (2.91 mm) of diethyl-2,6-dimethyl-4-(2-methylthiophenyl)-1,4-dihydropyridine-3,5-dicarboxylate 33 in 35 mL of dry $CH_2Cl_2$ was stirred at −78° C. under Ar and treated with 650 mg (3.20 mm) of m-chloroperbenzoic acid. After 1 hour the reaction was diluted with $CH_2Cl_2$ (150 mL) and washed with 10% aqueous sodium thiosulfate, $H_2O$, and brine, dried (anhydrous $MgSO_4$), filtered and concentrated to give 1.10 g of crude sulfoxide 34 (100%) used without purification for the following step.

Analytical sample obtained by crystallization from MeOH, m.p. 232°–3° C. Diethyl-1,4-dihydro-2,6-dimethyl-4-(2-(methylsulfinyl)phenyl-3,5-pyridinedicarboxylate (34). $^1H$ NMR (360 MHz, $CDCl_3$) δ=1.20, 1.22 (t, J=7.5 Hz, 3H, $CH_2CH_3$); 2.30, 2.32 (s, 3H each, $CH_3$); 2.82 (s, 3H, $S(O)CH_3$); 4.00–4.24 (m, 4H, $CH_2CH_3$); 5.45 (s, 1H, $ArCH$); 5.91 (bs, 1 Hz, NH); 7.38 (m, 3H, ArH); 8.00 (m, 1H, ArH).

m.p. 232°–3° C.

Step 2: Diethyl-4-[2-[[(acetyloxy)methyl]thio]phenyl]-1,4-dihydro-2,6-dimethyl-3,5-pyridinedicarboxylate (35)

A suspension of 3.31 g (8.46 mm) of sulfoxide 34 and NaOAc (anhydrous, 1.10 g) in 9.1 mL of acetic-anhydride was stirred at reflux for 40 minutes. The acetic anhydride was removed at reduced pressure, and the residue diluted with 250 mL of $CH_2CL_2$ and 50 mL of $H_2O$. The organic portion was washed with 10% aqueous HCl, 5% aqueous $NaHCO_3$, and brine, dried (anhydrous $MgSO_4$), filtered, evaporated, and flash chromatographed (silica gel, 30% EtOAc in hexane) to give acetate 35 (1.60 g, 44%).

An analytical sample was obtained by recrystallization from ether/hexane.

35 $^1H$ NMR (360 MHz, $CDCl_3$) δ=1.19 (t, J=7.0 Hz, 6H, $CH_2CH_3$); 2.14 (s, 3H, $CH_3C(O)$); 2.28 (s, 6H, $CH_3$); 3.99–4.14 (m, 4H, $OCH_2$); 5.40 (s, 2H, $C(O)CH_2S$); 5.42 (s, 1H, ArCH); 5.56 (bs, 1H, NH); 7.13 (dq, J=2.0, 7.5 Hz, 1H, ArH); 7.14 (dq, J=2.0, 7.5 Hz, 1H, ArH); 7.37 (dd, J=7.5, 2.0 Hz, 1H, ArH); 7.49 (dd, J=7.5, 2.0 Hz, 1H, ArH).

m.p. 117°–118° C.

Step 3: Diethyl-3,6-dihydro-2,4-dimethyl-2,6-methano-2H-1,3-benzothiazocine-5,11-dicarboxylate (36&37)

An absolute ethanol (30 mL) solution of 1.00 g (2.31 mm) of 35 was degassed with Ar and treated with anhydrous $K_2CO_3$ (2.20 g). After 3 hours of stirring under Ar, saturated aqueous $NH_4Cl$ was added and the mixture extracted with $CH_2CL_2$. The organic portions were washed with $H_2O$ and brine, dried (anhydrous $MgSO_4$), filtered and concentrated. Flash chromatography (silica gel, 2.5% acetone in $CH_2Cl_2$) separated the two diastereomers which crystallized from ether/hexane.

36 (isomer A) Fast: $^1H$ NMR (360 MHz, $CDCl_3$) δ=1.03 (t, J=7.0 Hz, 3H, $CH_2CH_3$); 1.33 (t, J=7.0 Hz, 3H, $CH_2CH_3$); 1.96 (s, 3H, $SCCH_3$); 2.23 (s, 3H, $CH_3$); 2.96 (d, J=4.5 Hz, 1H, $HCCO_2$); 3.90–4.25 9m, 4H, $OCH_2$); 4.64 (bs, 1H, N—H); 4.67 (d, J=4.9 Hz, 1H, ArCH); 6.92–7.05 (m, 3H, ArH); 7.44 (dd, J=7.5, 1.0 Hz, 1H, ArH).

37 (isomer B) Slow: $^1H$ NMR (360 MHz, $CDCl_3$) δ=1.26, 1.32 (t, J=7.5 Hz, 3H each, $OCH_2CH_3$); 1.90 (s, 3H, $SCCH_3$); 2.24 (s, 3H, $CH_3$); 3.02 (dd, J=1.5, 1.7 Hz; $HCCO_2$); 4.18–4.24 (m, 4H, $OCH_2$); 4.55 (bs, 1H, ArCH); 4.75 (bs, 1H, N—H); 7.01 (m, 3H, ArH); 7.50 (d, J=8.0 Hz, 1H, ArH).

m.p. 147°–148.5° C.

EXAMPLE 6

Diethyl 1,3,4,7-tetrahydro-3,5-dimethyl-3,7-methano-2,4-benzothiazonine-6,12-dicarboxylate (42&43)

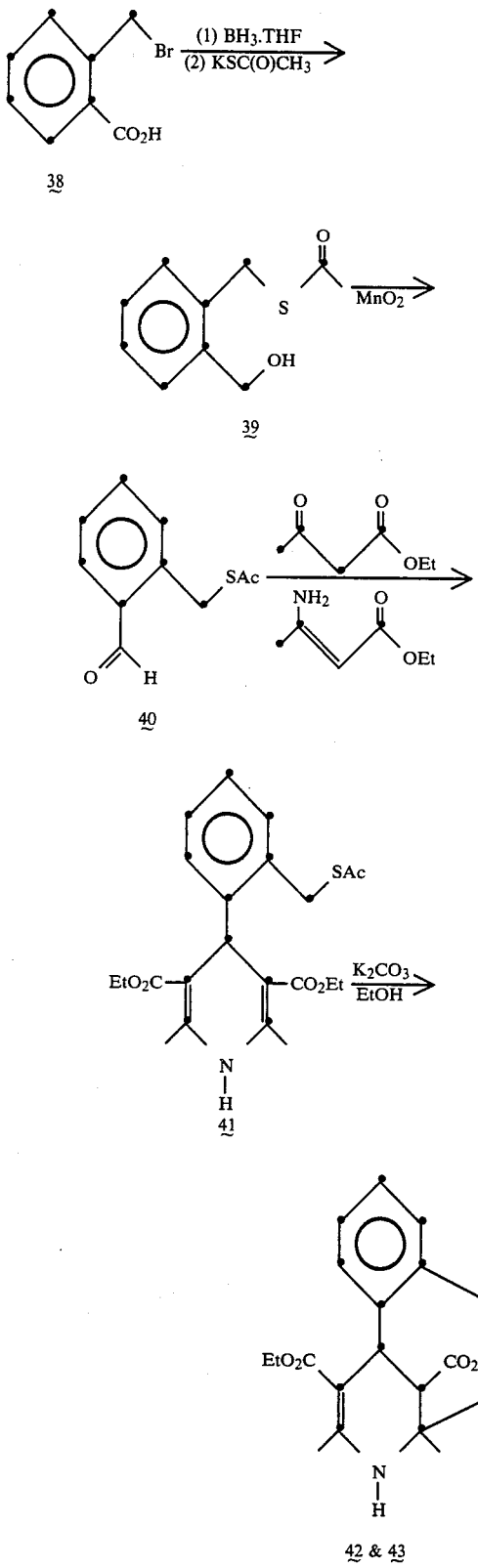

Step 1: Diethyl 4-[2-[(acetyl)thio]phenyl]-1,4-dihydro-2,6-dimethyl-3,5-pyridinedicarboxylate (41)

A solution of 2.00 g (9.30 mm) of o-(a-bromomethyl)-benzoic acid 38 (Shawnee Chem.Co.) in 10 mL of dry THF was stirred under Ar at 0° C. while 14.6 mL (14.6 mm) of 1.0M $BH_3$.THF was added dropwise. This mixture was stirred for 1.5 hours at 0° C., warmed to 25° C., and stirred an additional 0.5 hour. Water was added at 0° C. to quench the reaction followed by saturated aqueous sodium potassium tartrate. After extraction with ethyl acetate, the organic portion was washed with $H_2O$ and brine, dried (anhydrous $MgSO_4$), filtered and concentrated.

The crude product was treated directly with anhydrous DMF (8 mL) and stirred while 1.42 g of potassium thioacetate was added. After 10 minutes at 25° C., $H_2O$ was added and the mixture was extracted with ethyl acetate. The organic portion was dried (anhydrous $MgSO_4$), filtered, and evaporated to give crude alcohol 39 (2.00 g).

The crude alcohol 39 was dissolved in 100 mL of $CH_2Cl_2$ and stirred with 6.00 g of activated $MnO_2$ for 5 days. Filtration through Celite and evaporation afforded 1.40 g of aldehyde 40.

Aldehyde
40 'H NMR (90 MHz, $CDCl_3$) δ=2.25 (s, 3H, $CH_3$C(O)); 4.45 (s, 2H, $CH_2$S); 7.00–7.90 (m, 4H, Ar$\underline{H}$); 10.15 (s, 1H, C$\underline{H}$O).

Alcohol Crude:
39 'H NMR (90 MHz, $CDCl_3$) δ=2.25 (s, 3H, $CH_3$C(O)); 4.15 (s, 2H, S$\underline{CH_2}$); 4.70 (s, 2H, $\underline{CH_2}$O); 5.4 (s, 1H, O$\underline{H}$); 7.0–9.2 (m, 4$\underline{H}$, Ar$\underline{H}$).

1.40 Gram of aldehyde 40 was refluxed in isopropyl alcohol (10 mL) with 930 mg of ethyl aminocrotonate and 930 mg of ethyl acetoacetate under Ar for 24 hours. This was concentrated and flash chromatographed (silica gel, 2.5% acetone in $CH_2Cl_2$) to give: 500 mg 41.

41 'H NMR (90 MHz, $CDCl_3$), δ=1.20 (t, J=7.5 Hz, 6H, $CH_2CH_3$), 2.30 (s, 6H, $CH_3CN$); 2.39 (s, 3H, $CH_3$C(O)); 4.15 (q, J=7.5 Hz, 4$\underline{H}$, OC$\underline{H_2}$); 4.55 (s, 2$\underline{H}$, S$\underline{CH_2}$); 5.30 (s, 1H, ArC$\underline{H}$); 5.60 (bs, 1H, N$\underline{H}$; 7.00–7.40 (m, 4H, ArH).

Step 2: Diethyl 1,3,4,7-tetrahydro-3,5-dimethyl-3,7-methano-2,4-benzothiazonine-6,12-dicarboxylate (42&43)

A mixture of 5.20 g of dihyropyridine 41, 15.0 g of anhydrous potassium carbonate, and 150 mL of degassed absolute ethanol was vigorously stirred under an Ar atmosphere for 12 hours. Saturated aqueous $NH_4Cl$ was added, and the whole was extracted with ethylacetate. The organic portion was washed with $H_2O$, and brine, dried (anhydrous $MgSO_4$), filtered, and flash chromatographed (silica gel, 2% acetone in $CH_2Cl_2$) to afford 42 and 43.

42 'H NMR (360 MHz, $CDCl_3$) δ=1.12, 1.27 (t, J=7.0 Hz, 3H each, $CH_2$—$CH_3$); 1.57 (S, 3H, S—C—C$\underline{H}$); 2.45 (s, 3H, $CH_3$); 3.33 (d, J=15.0 Hz, 1H, S—C$\underline{H}$aHb); 3.47 (bs, 1H, H $CO_2$); 3.94 (m, 2H, OC$\underline{H_2}$); 4.17 (m, 2H, OC$\underline{H_2}$); 4.24 (bs, 1H, ArC$\underline{H}$); 4.62 (bs, 1H, N$\underline{H}$); 4.73 (d, J=15.0 Hz, 1H, S—C$\underline{H}$aHb); 6.95 (dd, J=1.0, 7.0 Hz, 1H, Ar$\underline{H}$); 7.08 (dt, J=1.0, 7.0 Hz, 1H, Ar$\underline{H}$); 7.16 (dt, J=1.0, 7.0 Hz, 1H, Ar$\underline{H}$); 7.33 (dd, J=1.0, 7.0 Hz, 1H, Ar$\underline{H}$).

43 'H NMR (360 MHz, $CDCl_3$) δ=1.14, 1.17 (t, J=7.0 Hz, 3H each, $CH_2CH_3$); 1.69 (S, 3H, SCC$\underline{H_3}$); 2.42 (S, 3H, CH$_3$); 3.18 (d, J=6.0 Hz, 1H, HCO$_2$); 3.27 (d, J=15.0 Hz, 1H, SCHaHb); 3.99 (M, 2H, CH$_2$CH$_3$); 4.47 (bs, 1H, N—H); 4.56 d, J=15.0 Hz, 1H, SCHaHb); 4.65 (d, 5=6.0 Hz, 1H, ArCH); 6.94 (dd, J=1.0, 7.0 Hz, 1H, ArH); 7.04 (dt, J=1,0, 7.0 Hz, 1H, ArH); 7.08 (dt, J=1,0, 7.0 Hz, 1H, ArH); 7.27 (dd, J=1.0, 7.0 Hz, 1H, ArH).

EXAMPLE 7

Diethyl 1,3,4,7-tetrahydro-3,5-dimethyl-9-(trifluoromethyl-3,7-methano-2,4-benzothiazocine-6,12-dicarboxylate (47&48)

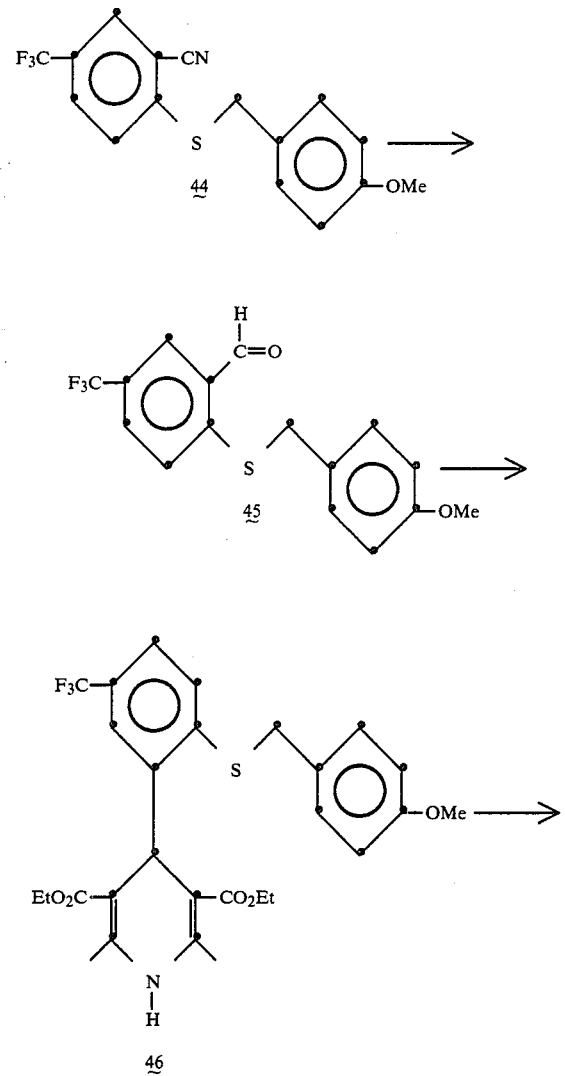

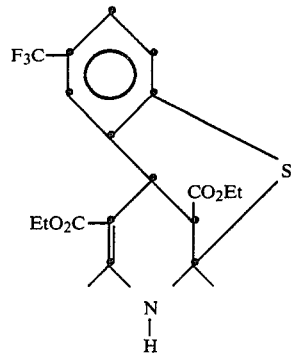

47 & 48

Step 1

A cold (−78° C.) anhydrous methylene chloride (90 mL) solution of nitrile 44 (28.0 g, 86.6 mm) was stirred while 87 mL of 1.0M diisobutylaluminum hydride in Hexane (87 mm) was added dropwise over 15 minutes. This was stirred an additional 1.0 h at −78° C. then allowed to reach 25° C. The mixture was recooled to −78° C. and treated with 20 mL of methanol and 50 mL of saturated sodium potassium tartrate. After warming to 25° C., ethyl acetate was added and the mixture was stirred while 2.4N HCl was added to acidify the aqueous layer. After stirring for 1 hour at room temperature, the organic portion was separated and the aqueous portion was extracted with ethyl acetate. The combined organic portions were washed with H$_2$O, and brine, dried (anhydrous MgSO$_4$), filtered and concentrated. The oil crystalized from ether/hexane (1/1) to afford 26.0 grams of a white solid 45 (92%). a-(4methoxy-a-toluenylthio)-5-(trifluoromethyl)benzaldehyde: 1H NMR (90 MHz, CDCl$_3$) δ=3.75 (S, 3H, OCH$_3$); 4.12 (S, 2H, SCH$_2$), 6.7–8.0 (multiplets, 7H, ArH); 10.15 (S, 1H, CHO).

Step 2

23.1 g (70.8 mm) of aldehyde 45, 9.20 g of methyl acetoacetate and 9.20 g of ethylaminocrotonate were refluxed in 30 mL of isopropylalcohol for 20 hours. After cooling to 25° C. and evaporation of the solvents, a white solid precipitated from ether. This was washed with ether/hexane (1:1) to give 23.0 grams of 46.
46 diethyl-1,4-dihydro-4-(2-(4-methoxy-a-toluenylthio)5-(trifluoromethyl)phenyl)-2,6-dimethylyl-3,5-pyridine dicarboxylate 'H NMR (90 MHz, CDCl$_3$) δ1.15 (t, J=7.5 Hz, 6H, CH$_2$CH$_3$); 3.70 (S, 3H, OCH$_3$); 3.95 (q, J=7.5 Hz, 4H, OCH$_2$); 4.05 (S, 2H, SCH$_2$); 5.35 (S, 1H, Aryl. CH); 5.73 (bs, 1H, N—H); 6.70–7.50 (m, 7H, Ar—H).

Step 3

A solution of 2.20 grams of 46 was dissolved in 10 mL of anisole and degassed with Ar for 15 minutes. This was stirred while 10 mL of trifluoroacetic acid was added dropwise over 2 minutes at 25° C. After 15 minutes, the reaction was complete and the mixture diluted with CH$_2$Cl$_2$ and washed with H$_2$O, and saturated aqueous NaHCO$_3$, dried (anhydrous MgSO$_4$), filtered and concentrated. Th two diastereomers formed were separated by flash chromatography (silica gel, CH$_2$Cl$_2$, then 2.5% acetone in CH$_2$Cl$_2$). After concentration of appropriate fractions the pure diastereomers were crystallized from ether/hexane to afford the 47 and 48 isomers.

Yield: 500 mgs of the fast diastereomer 47, 350 mgs of the slow diastereomer 48, and 1.00 gr of a mixture of 47 and 48.

47 $^1$H NMR (CDCl$_3$), 360 mHz) $\delta$=1.01 and 1.35 (t, J=7.5 Hz, 3H each, CH$_2$C$\underline{H}_3$); 1.97 (S, 3H, S—C—C$\underline{H}_3$); 2.25 (S, 3H, CC$\underline{H}_3$); 3.00 (d, J=4.5 Hz, 1H, $\underline{H}$CCOz); 3.92–4.27 (m, 4H, OC$\underline{H}_2$); 4.68 (d, J=4.5 Hz, 1H, 1H, ArC$\underline{H}$); 4.72 (bs, 1H, N—$\underline{H}$); 7.13 (d, J=7.5 Hz, 1H, ArH); 7.24 (dd, J=7.5 Hz, 1.5H, 1H, ArH); 7.69 (d, J=1.5 Hz, 1H, ArH).

48 1H NMR (CDCl$_3$, 360 MHz) $\delta$=1.27 and 1.34 (t, J=6.0 Hz, 3H each, CH$_2$C$\underline{H}_3$); 1.93 (S, 3H, SCC$\underline{H}_3$); 2.27 (S, 3H, C$\underline{H}_3$); 2.97 (dd, J=3.0, 1.5 Hz, 1H, $\underline{H}$CCO$_2$); 4.07–4.27 (m, 4H, OC$\underline{H}_2$); 4.58 (bs, 1H, ArC$\underline{H}$); 4.83 (bs, 1H, N$\underline{H}$); 7.13 (d, J=7.5 Hz, 1H, ArH; 7.27 (dd, J=7.5, 1.5 Hz, 1H, ArH); 7.76 (d, =1.5 Hz, 1H, ArH).

EXAMPLE 8

Diethyl 1,3,4,7-tetrahydro-3,5-dimethyl-8-nitro-3,7-methano-2,4-benzothiazocine-6,12-dicarboxylate (53&54)

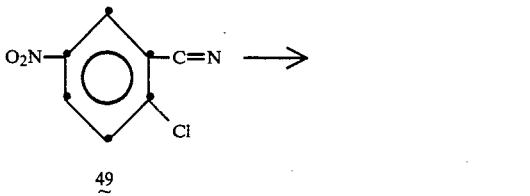

49

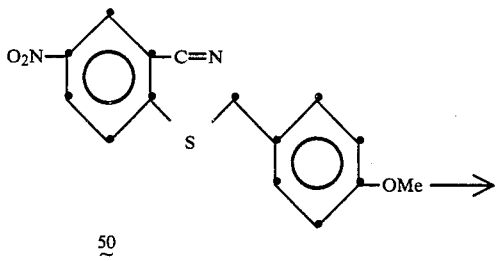

50

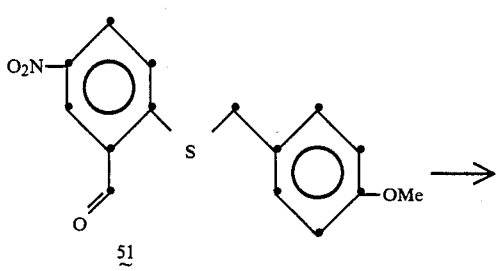

51

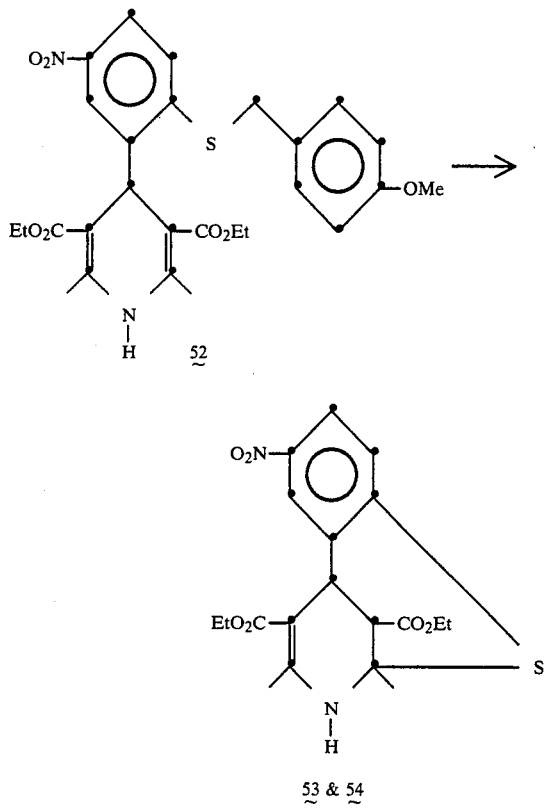

52

53 & 54

Step 1

A solution of 0.84 g of p-methoxy-a-toluenethiol (5.45 mm) in 15 mL of degassed methanol cooled to 0° C. was stirred while 393 mg of sodium methoxide was added. After stirring for 10 minutes, 1.03 g (5.64 mm) of 2-chloro-5-nitrobenzonitrile 49 was added in one portion and this was allowed to stir for 1 hour at 0° C., then 2 hours at 25° C. This mixture was then diluted with H$_2$O (60 mL) and stirred 5 minutes. The solid precipitate that formed was collected by filtration and washed with H$_2$O. This was dried at 80° C. (1 mm) for 12 hours from which 49 was removed by sublimation. The remaining yellow solid, 2-(4-methoxy-a-toluenethio)-5-nitro-benzonitrile 50 (1.40 g, 77% yield) was used without further purification for the next step.

50 1H NMR (90 MHz, CDCl$_3$) $\delta$=3.80 (S, 3H, OC$\underline{H}_3$); 4.30 (S, 2H, SC$\underline{H}_2$); 6.80–7.60 (m, 5H, ArH); 8.30 (dd, J=3.0, 9.0 Hz, 1H, ArH); 8.45 (d, J=3.0 Hz, 1H, ArH).

Step 2

Nitrile 50 was reduced in the same manner as compound 44 (Example 7) to give aldehyde 51 as a yellow solid in 65% yield.

51 2-(4-methoxy-a-toluenethio)-5-nitrobenzaldehyde: $^1$H NMR (90 MHz, CDCl$_3$) $\delta$=3.80 (S, 3H, OC$\underline{H}_3$); 4.30 (S, 2H, SC$\underline{H}_2$); 6.90 (d, J=8.0 Hz, 2H, Ar$\underline{H}$); 7.39 (d, J=8.0 Hz, 2H, ArH); 7.58 (d, J=9.0 Hz, 1$\underline{H}$, ArH); 8.32 (dd, J=9.0, 3.0 Hz, 1H, ArH); 8.68 (d, J=3.0 Hz, 1H, ArH); 10.38 (S, 1H, C$\underline{H}$O).

Step 3

Aldehyde 51 was condensed in a similar manner to compound 45 (Example 7) to provide dihydropyridine 52 after crystallization from ether/hexane/CH$_2$Cl$_2$ in 50% yield.

52 diethyl 1,4-dihydro-4-(2-(4-methoxy-a-toluenylthio)-5-nitrophenyl)-2,b-dimethyl-3,5-pyridinedicarboxylate: 'H NMR (70 MHz, CDCl$_3$): δ=1.10 (t, J=7.5 Hz, 6H, CH$_2$C$\underline{H}_3$); 2.22 (S, 6H, C$\underline{H}_3$); 6.77 (S, 3H, OC$\underline{H}_3$); 4.03 (q, J=7.5 Hz, 4H, OC$\underline{H}_2$); 4.14 (S, 2H, SC$\underline{H}_2$); 5.40 (S, 1H, ArC$\underline{H}$); 5.68 (bs, 1H, N$\underline{H}$); 7.79 (d, J=8.0 Hz, 2H, Ar$\underline{H}$); 7.23 (m, 3H, Ar$\underline{H}$); 7.81 (dd, J=3.0, 9.0 Hz, 1H, Ar$\underline{H}$); 8.08 (d, J=3.0 Hz, 1H, ArH).

Step 4

5.4 grams of dihydropyridine 52 was treated similarly to dihydropyridine 46 (Example 7) to provide two diastereomeric benzothiazocines 53 and 54 which were separated by flash chromatography (silica gel, 2.5% acetone in methylene chloride) to give, after crystallization, the isomers 53 and 54.

53 'H NMR (360 MHz, CDCl$_3$) δ=1.07 and 1.41 (t, J=7.5 Hz) 3H each, CH$_2$C$\underline{H}_3$); 1.98 (S, 3H, SCC$\underline{H}_3$); 2.26 (S, 3H, C$\underline{H}_3$); 3.05 (d, J=4.5 Hz, 1H, HCC$\underline{O}_2$); 3.90–4.30 (m, 4H, OC$\underline{H}_2$); 4.73 (d, J=4.5 Hz, 1H, ArC$\underline{H}$); 4.77 (bs, 1H, N$\underline{H}$); 7.16 (d, J=9.0 Hz, 1H, Ar$\underline{H}$); 7.88 (dd, J=3.0, 9.0 Hz) 1H, ArH); 8.33 (d, J=3.0 Hz, 1H, Ar$\underline{H}$).

54 'H NMR (360 MHz, CDCl$_3$) δ=1.28, 1.39 (t, J=7.5 Hz, 3H each, CH$_2$C$\underline{H}_3$); 1.96 (S, 3H, SCC$\underline{H}_3$); 2.28 (S, 3H, C$\underline{H}_3$); 2.96 (dd, J=2.0, 1.5 Hz, 1H, HCC$\underline{O}_2$); 4.09–4.28 (m, 4H, OC$\underline{H}_2$); 4.64 (bs, 1H, ArC$\underline{H}$); 4.87 (bs, 1H, N$\underline{H}$); 7.15 (d, J=9.0 Hz, 1H, Ar$\underline{H}$); 7.90 (dd, J=3.0, 9.0 Hz, 1H, Ar$\underline{H}$); 8.38 (d, J=3.0 Hz, 1H, Ar$\underline{H}$).

EXAMPLE 9

Dimethyl 8-(2,4-difluorophenyl)-3,6-dihydro-2,4-dimethyl-2,6-methano-2H-1,3-benzoxazocine-5,11-dicarboxylate (61&62)

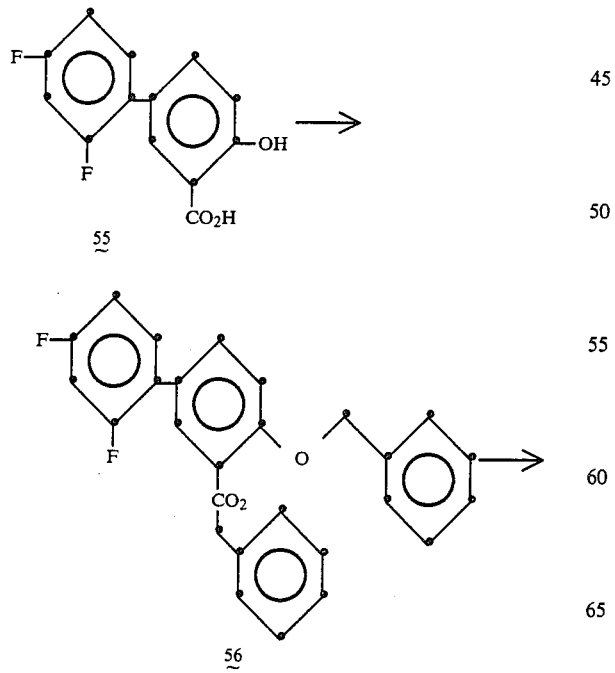

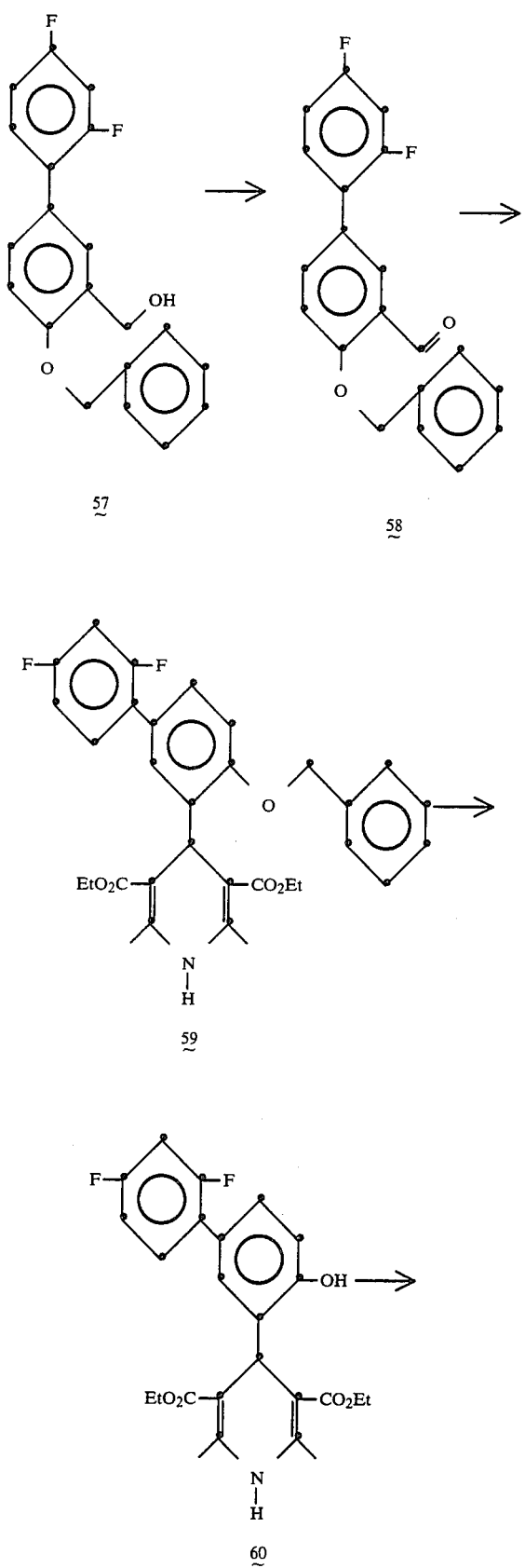

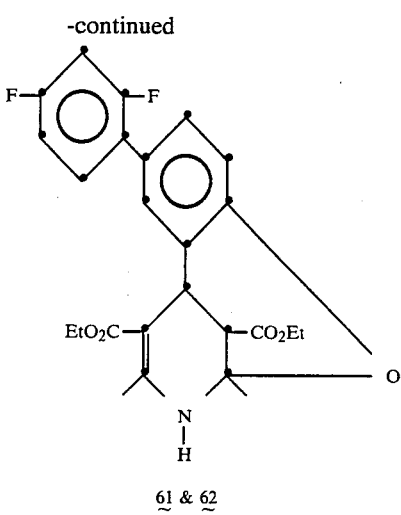

61 & 62

Step 1

A solution of 2',4'-difluoro-4-hydroxy (1,1'-biphenyl)-3-carboxylic acid 55 (1.00 g, 4.00 mm) in 8 mL of dimethylformamide was stirred at 25° C. and treated with 5.52 g (40.00 mm) of powdered potassium carbonate and 1.2 mL of benzyl bromide (10.0 mm). After 24 hours, the mixture was diluted with $H_2O$ and extracted with ethyl acetate. The organic portion was washed with $H_2O$ and brine, dried (anhydrous $MgSO_2$), filtered and evaporated to yield, after crystallization from ether/hexane, 1.50 g of 56 as a white solid (81%).

56 benzyl 2',4'-difluoro-4-benzyloxy(1,1'-bipenyl)-3-carboxylate. $^{1}H$ NMR (90 MHz, $CDCl_3$)δ=5.20 (S, 2H, $OCH_2$); 5.40 (S, 2H, O $CH_2$); 6.8–7.2 (m, 15H, Ar$H$); 7.97 (m, 1H, Ar$H$).

Step 2

56 (7.25 g, 16.86 mm) was dissolved in 125 mL of anhydrous tetrahydrofuran and diethyl ether (⅓), stirred at 0° C. under Ar, and treated with lithium aluminum hydride (641 mg, 16.86 mm). After 1 hour the reaction was quenched with 10% aqueous tetrahydrofuran and then dried (anhydrous $MgSO_4$), filtered and concentrated to give 5.25 g (92%) of a white solid 57 after recrystallization from ether/hexane.

57 2-benzyloxy-5-(2,4-difluorophenyl)benzylalcohol: $^{1}H$ NMR (90 MHz, $CDCl_3$)δ=2.27 (t, J=6.0 Hz, 1H, O$H$); 4.82 (d, J=6.0 Hz, 2H, $CH_2OH$); 5.18 (S, 2H, $CH_2$); 6.70–6.90 (m, 3H, Ar$H$); 7.40 (M, 8H, Ar$H$).

Step 3

A methylene chloride (200 mL) solution of alcohol 57 (5.25 g) was stirred with 15.0 g of activated $MnO_2$ for 60 hours at 25° C. After filtration and concentration aldehyde 58 was obtained (3.20 g, 61%) as a white solid.

58 2',4'-difluoro-4-benzyloxy(1,1'-biphenyl)-3-carboxaldehyde. $^{1}H$ NMR (90 MHz $CDCl_3$)δ=5.25 (S, 2H, $OCH_2$); 6.75–7.75 (m, 10H, Ar$H$); 8.00 (d, J=3 Hz, 1H, Ar$H$); 10.60 (S, 1H, $CHO$). m.p. 124.0°–125.5° C.

Step 4

3.00 g of 58 was condensed under similar conditions as aldehyde 45 to give 3.00 g of dihydropyridine 59 after recrystallization from ether/hexane.

59 diethyl 1,4-dihydro-4-(2-benzyloxy-5-(2,4-difluorophenyl)phenyl)-2,6-dimethyl-3,5-pyridine-dicarboxylate: $^{1}H$ NMR (90 MHz, $CDCl_3$)δ=1.10 (t, J=7.0 Hz, 6H, $CH_2CH_3$); 2.05 (S, 6H, $CH_3$); 4.03 (q, J=7.0 Hz, 4H, $OCH_2CH_3$); 4.80 (bs, 1H, N$H$); 5.00 (S, 2H, $OCH_2Ar$); 5.25 (S, 1H, Ar$CH$); 6.90–7.50 (m, 11H, Ar$H$).

Step 5

An absolute ethanol solution of dihydropyridine 59 (2.66 g in 100 mL) was charged with 210 mg of 5% Pd on carbon and shaken under 1 Atm of $H_2$ for 4 days. This was filtered and concentrated to give the phenol 60 (2.40 g).

60 diethyl 1,4-dihydro-4-(5-(2,4-difluorophenyl)-2-hydroxyphenyl)-2,6-dimethyl-3,5-pyridine dicarboxylate: $^{1}H$ NMR (90 MHz, $CDCl_3$)δ=1.20 (t, J=7.5 Hz, 6H, $CH_2CH_3$); 2.35 (S, 6H, $CH_3$); 4.10 (q, 5=7.5 Hz, 4H, $OCH_2$); 5.15 (S, 1H, Ar$CH$); 6.10 (bs, 1H, N$H$); 6.70–7.45 (m, 6H, Ar$H$); 9.05 (bs, 1H, O$H$).

Step 6

Phenol 60 was treated in a similar manner to compound 17 (Example 1) to give, after flash chromatography (silica gel, 2.5% acetone in methylenechloride) and concentration of appropriate fractions, the two title diastereomeric benzoxazocines 61 and 62 as white solids (from ether/hexane).

61 $^{1}H$ NMR (360 MHz, $CDCl_2$)δ=1.13, 1.33 (t, J=7.5 Hz, 3H each, $CH_2CH_3$); 1.88 (S, 3H, $OCCH_3$); 2.21 (S, 3H, $CH_3$); 2.83 (d, J=3 Hz, $HCCO_2$); 4.09 (q, J=7.5 Hz, 2H, $OCH_2$); 4.10–4.30 (m, 2H, $OCH_2$); 4.54 (d, J=3.0 Hz, 1H, Ar$CH$); 4.89 (bs, 1H, N$H$); 6.87 (m, 3H, Ar$H$); 7.22 (dt, J=8.0 Hz, 2.0 Hz, 1$H$, Ar$H$); 7.36 (dt, J=7.0, 8.0 Hz, 1N, Ar$H$); 7.53 (bs, 1H, Ar$H$).

62 $^{1}H$ NMR (360 MHz, $CDCl_3$)δ=1.25, 1.32 (t, J=7.5 Hz, 3H each, $CH_2CH_3$); 1.93 (S, 3H, $OCCH_3$); 2.24 (S, 3H, $CH_3$); 3.00 (dd, J=3.0, 1.5 Hz, 1H, $HCCO_2$, collapses to doublet J=3.0 Hz upon irradiation at 4.97 ppm); 4.05–4.26 (m, 4H, $OCH_2$); 4.64 (d, J=3.0 Hz, 1H, Ar$CH$); 4.97 (bs, 1H, N$H$); 6.89 (m, 3H, Ar$H$); 7.22 (dt, 5=8.0 Hz, 1.5 Hz, 1$H$, Ar$H$); 7.35 (dt, J=7.0, 9.0 Hz, 1H, Ar$H$); 7.53 (t, J=1.5 Hz, 1H, Ar$H$).

EXAMPLE 10

Diethyl 3,6-dihydro-2,4-dimethyl-10-nitro-2,6-methano-2H-1,3-benzothiazocine-5,11-dicarboxylate (68&69)

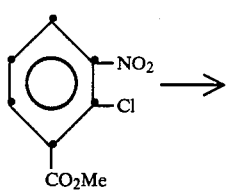

63

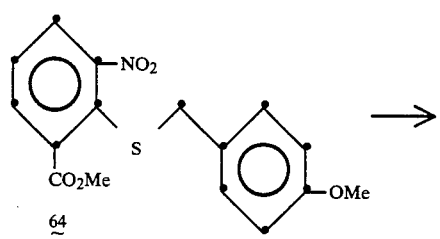

64

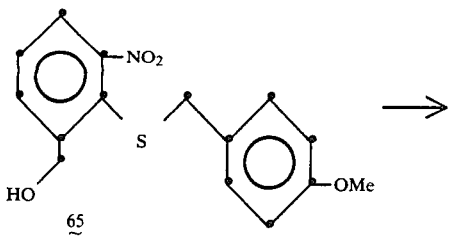

65

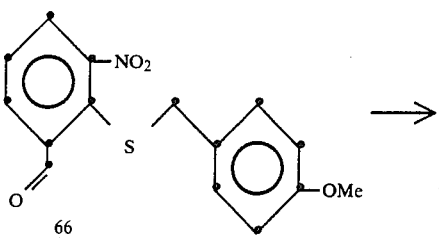

66

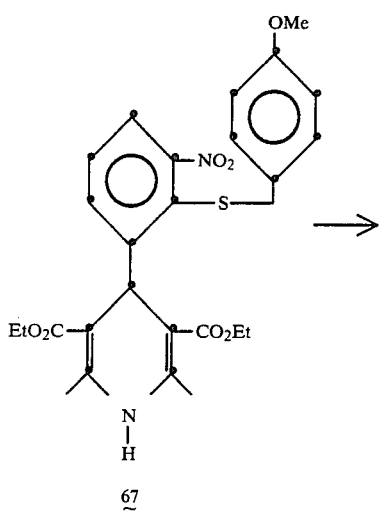

67

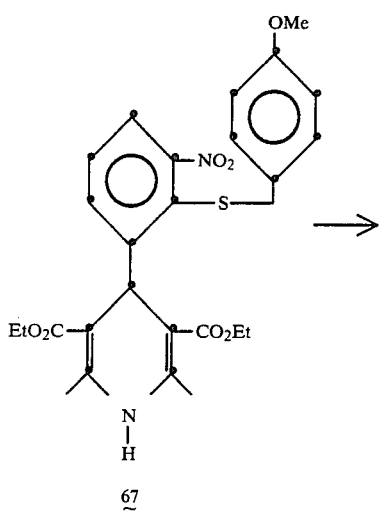

68 & 69

Step 1

An anhydrous dimethylformamide (DMF) solution of p-methoxy-a-toluenethiol (1.86 mL in 15 mL of DMF) was cooled to 0° C. under Ar and 106 mg (13.37 mm) of lithium hydride was added. This stirred suspension was warmed to 25° C. for 20 minutes and then methyl 2-chloro-3-nitrobenzoate 63 was added in one portion. An exothermic reaction took place and was cooled to 0° C. The mixture was rewarmed to 25° C. and stirred for 10 minutes, diluted with H$_2$O, and extracted with ethyl acetate. The organic portion was washed with H$_2$O and brine, dried (anhydrous MgSO$_4$), filtered, concentrated and flash chromatographed (silica gel, 50% ether in hexane). After concentration of appropriate fractions, 2.80 g (75%) of 64 as a yellow oil was obtained.

64 Methyl 2-(p-methoxy-a-toluenylthio)-3-nitrobenzoate: 1H NMR (90 MHz, CDCl$_3$)δ=3.73, 3.90 (S, 3H each) OCH$_3$); 4.08 (S, 2H, SCH$_2$); 6.7–7.8 (m, 7H, ArH).

Step 2

The methyl benzoate 64 was treated similarly to compound 44 (Example 7) with diisobutyl aluminum hydride at −78° C. The crude product 65 was isolated as a yellow oil in 96% yield.

65 2-(p-methoxy-a-toluenethio)-3-nitrobenzyl alcohol: 'H NMR (90 MHz, CDCl$_3$)δ=2.20 (bt, J=5.0 Hz, 1H, OH); 3.74 (S, 3H, OCH$_3$); 3.95 (S, 2H, SCH$_2$); 4.63 (bd, J=5.0 Hz, 2H, OCH$_2$); 6.68–7.70 (m, 7H, ArH).

Step 3

Treatment of alcohol 65 under conditions similar to alcohol 57 (Example 9) gave an 80% yield of 66 as a yellow solid from ether/hexane.

66 1-(p-methoxy-a-toluenethio)-2-nitrobenzaldehyde: 'H NMR (90 MHz, CDCl$_3$)δ=3.80 (S, 3H, OCH$_3$); 4.00 (S, 2H, SCH$_2$); 6.70–7.10 (m, 4H, ArH); 7.50–8.10 (m, 3H, ArH); 10.20 (s, 1H, CHO). m.p. 95.0°–97.5° C.

Step 4

Dihydropyridine 67 was obtained from aldehyde 66 by the same conditions as used for dihydropyridine 59 (Example 9). 67 crystallized from ether/hexane as a yellow solid.

67 Diethyl 1,4-dihydro-4-(2-(((4-methoxyphenyl)methyl)thio)-3-nitrophenyl)-2,6-dimethyl-3,5-pyridinedicarboxylate: 'H NMR (360 MHz, CDCl$_3$)δ=1.17 (t, J=7.5 Hz, 6H, CH$_2$CH$_3$); 2.27 (S, 6H, CH$_3$); 3.80 (S, 3H, OCH$_3$); 4.07 (S, 2H, SCH$_2$); 4.08 (m, 4H, OCH$_2$); 5.59 (bs, 1H, NH); 5.81 (S, 1H, ArCH); 6.84 (d, J=8.0 Hz, 2H, ArH); 7.33 (d, J=8.0 Hz, 2H, ArH); 7.34 (m, zH, ArH); 7.62 (dd, J=7.5, 1.5 Hz, 1H, ArH).

Step 5

Dihydro pyridine 67 was reacted under conditions similar to dihydropyridine 52 (Example 8) to give the two benzothiazocine diastereomers 68 and 69 which were separated by flash chromatography (silica gel, 2.5% acetone in methylene chloride) and crystallized from ether/hexane.

68 'H NMR (360 MHz, CDCl$_3$)δ=1.05, 1.31 (t, J=7.5 Hz, 3H each, CH$_2$CH$_3$); 1.96 (S, 3H, SCCH$_3$); 2.24 (S, 3H, CH$_3$); 3.01 (d, J=4.0 Hz, 1H, HCCO$_2$); 4.01 (q, J=7.5 Hz, 2H, OCH$_2$); 4.07–4.25 (m, 2H, OCH$_2$); 4.77 (d, J=4.0 Hz, 1H, ArCH); 4.80 (6S, 1H, NH); 7.11 (t, J=7.5 Hz, 1H, ArH); 7.76 (dd, J=7.5 Hz, 1.5 Hz, 1H, ArH); 8.07 (dd, J=7.5, 1.5 Hz, 1H, ArH).

69 'H NMR (360 MHz, CDCl$_3$)δ=1.27, 1.30 (t, J-7.5 Hz, 3H each, CH$_2$CH$_3$); 1.95 (s, 3H, SCCH$_3$); 2.26 (s, 3H, CH$_3$); 2.92 (t, J-1.5 Hz, 1H, HCCO$_2$); 4.05–4.25 (m, 4H, OCH$_2$); 4.68 (bs, 1H, ArCH); 4.68 (bs, 1H, NH); 7.14 (t, J=9.0 Hz, 1H, ArH); 7.82 (d, J=9.0 Hz, 1H, ArH); 8.07 (d, J=9.0 Hz, 1H, ArH).

EXAMPLE 11

Diethyl 3,6-dihydro-2,4-dimethyl-10-nitro-2,6-methano-2H-1,3-benzoxazocine-5,11-dicarboxylate (74&75)

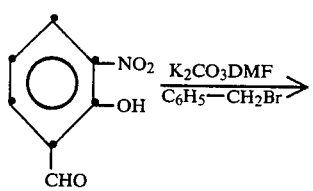

70

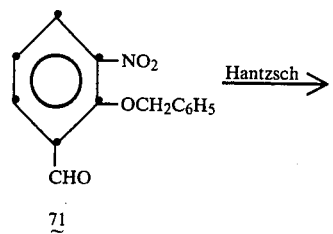

71

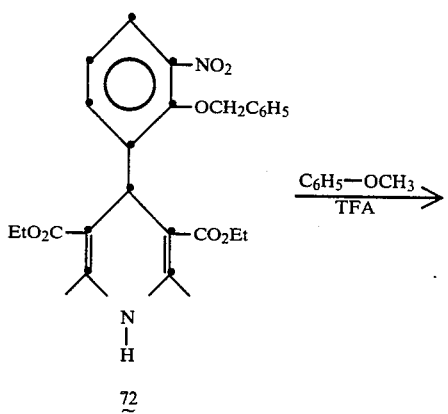

72

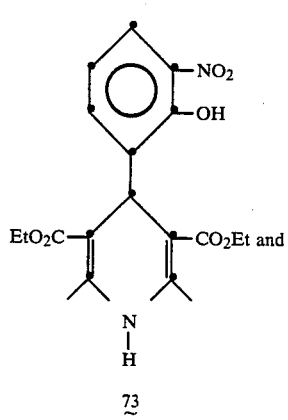

73

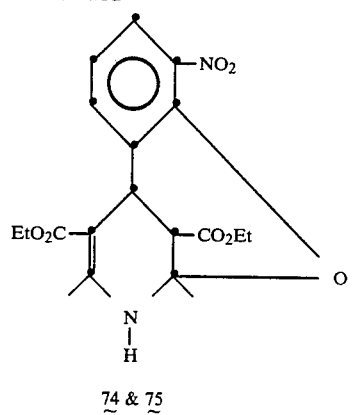

74 & 75

Step 1

A mixture of 70 (16.7 g, 0.1 mole), pulverized potassium carbonate (13.8 g, 0.1 mole), and benzyl bromide (48 ml, 0.4 mole) in DMF (100 ml) was stirred overnight at room temperature. H$_2$O was added and the separated solid was filtered off and washed with H$_2$O, then with ether and dried to yield 16.2 g (63%) of 71. Compound 71 was condensed under similar conditions to give the dihydropyridine 72.

71 $^1$H NMR (90 MHz, CDCl$_3$): δ5.2 (s, 2H, —OCH$_2$); 7.4 (s, 5H, C$_6$H$_5$); 7.4 (m, 1H, ArH); 8.0–8.2 (m, 2H, ArH), 10.25 (s, 1H, —CHO).

72 $^1$H NMR (360 MHz, CDCl$_3$): δ1.13 (t, J-7.5 Hz, 6H, —CH$_2$CH$_3$); 2.17 (s, 6H, —CH$_3$); 3.95–4.08 (m, 4H, —CH$_2$CH$_3$); 4.97 (s, 2H, —CH$_2$); 5.2 (bs, 1H, —NH); 5.35 (s, 1H, ArCH); 7.08 (t, J=7.5 Hz, 1H, ArH); 7.3–7.4 (m, 3H, ArH); 7.52 (bd, 2H, ArH); 7.58 (dd, J=1.5, 7.5 Hz, 1H, ArH); 7.69 (dd, J=1.5, 7.5 Hz, 1H, ArH). M.p. 147°–149° C.

Step 2

Anisole (5 ml) was degassed and then 72 (2 g) was added. The reaction mixture was protected from light and stirred under nitrogen as trifluoroacetic acid (5 ml) was added. The resulting yellow solution was stirred at room temperature for 15 minutes, a saturated solution of NaHCO$_3$ (5 ml) was added, and the mixture extracted with CH$_2$Cl$_2$. The extract was dried (Na$_2$SO$_4$), filtered and concentrated in vacuo to yield an oil which was a mixture of 73, 74 and 75. Flash chromatography (silica gel, 1:1 ether-hexanes) separated 73 from the mixture of 74 and 75. A solution of 73 in CHCl$_3$ containing a catalytic amount of dl-10-camphorsulfonic acid was stirred at room temperature for 15 minutes and then concentrated in vacuo. The residue, which contained a mixture of 73, 74 and 75 was chromatographed, and the recovered 73 was again reacted. This procedure provided a sufficient quantity of 74 and 75 to be obtained for separation and purification. The mixture of 74 and 75 was flash chromatographed (silica gel, 1:1 ether-hexanes) to yield 74 as a yellow solid (from ether) and 75 as a yellow solid (from ether). An analytical sample of 73 was obtained from ether.

73 $^1$H NMR (360 MHz, CDCl$_3$): δ1.19 (t, J=7.5 Hz, 6H, —CH$_2$CH$_3$); 2.32 (s, 6H, —CH$_3$); 4.0–4.15 (m, 4H, —CH$_2$CH$_3$); 5.35 (s, 1H, ArCH); 5.67 (bs, 1H, —NH); 6.85 (t, J=7.5 Hz, 1H, ArH); 7.6 (dd, J=1.5, 9 Hz, 1H, ArH); 7.95 (dd, J=1.5, 9 Hz, 1H, ArH). m.p. 150°–151° C.

74 (Fast isomer) 'H NMR (360 MHz, CDCl₃): δ1.25, 1.35 (t, J=7.5 Hz, 3H each, —CH₂CH₃); 1.98 (s, 3H, —OCCH₃); 2.23 (s, 3H, —CH₃); 2.97 (dd, J=3.0, 1.5 Hz, 1H, CHCO₂); 4.07–4.26 (m, 4H, —CH₂CH₃); 4.7 (d, J=3.0 Hz, 1H, ArCH); 5.13 (bs, 1H, —NH); 6.9 (t, J=7.5 Hz, 1H, ArH); 7.6 (dd, J=1.5, 7.5 Hz, 1H, ArH); 7.66 (dd, J=1.5, 7.5 Hz, 1H, ArH). m.p. 130°–139° C.

75 (Slow isomer) 'H NMR (360 MHz, CDCl₃): δ1.11, 1.35 (t, J=7.5 Hz, 3H each, —CH₂CH₃); 1.9 (s, 3H, OCCH₃); 2.21 (s, 3H, —CH₃); 2.87 (d, J=3.0 Hz, 1H, CHCO₂); 4.05–4.28 (m, 4H, —CH₂CH₃); 4.55 (d, J=3.0 Hz, 1H, ArCH); 5.04 (bs, 1H, —NH); 6.9 (t, J=7.5 Hz, 1H, ArH); 7.58 (dd, J=1.5, 7.5 Hz, 1H, ArH); 7.66 (dd, J=1.5, 7.5 Hz, 1H, ArH). m.p. 168°–169° C.

EXAMPLE 12

Diethyl 3,6-dihydro-2,4-dimethyl-9-nitro-2,6-methano-2H-1,3-benzoxazocine-5,11-dicarboxylate (77&78)

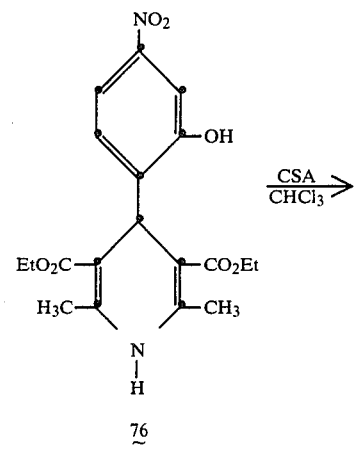

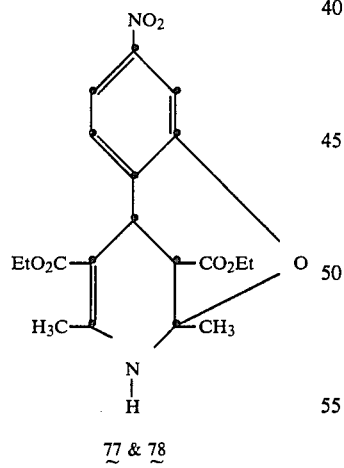

Phenol 76 was prepared in a similar fashion to phenol 17 (Example 1).

76 'H NMR (90 MHz, CDCl₃): δ1.2 (t, J=7.5 Hz, 6H, —CH₂CH₃); 2.35 (s, 6H, —CH₃); 4.1 (q, J=7.5 Hz, 4H, —CH₂CH₃); 5.1 (s, 1H, ArCH); 6.2 (bs, 1H, NH); 7.1–7.7 (m, 3H, ArH); 9.4 (bs, 1H, —OH).

Benzoxazocines 77 and 78 were prepared simarlarly to 18 and 19 (Example 1).

77 Fast isomer 'H NMR (360 MHz, CDCl₃): δ1.25, 1.35 (t, J=7.5 Hz, 3H each, —CH₂CH₃); 1.93 (s, 3H, OCCH₃); 2.22 (s, 3H, —CH₃); 2.95 (dd, J=1.5, 3.0 Hz, 1H, CHCO₂); 4.07–4.26 (m, 4H, —CH₂CH₃); 4.7 (d, J=3.0 Hz, 1H, ArCH); 5.05 (bs, 1H, —NH), 7.5 (d, J=9.0 Hz, 1H, ArH); 7.65 (d, J=3.0 Hz, 1H, ArH), 7.7 (dd, J=3.0, 9.0 Hz, 1H, ArH). m.p. 144°–147° C.

78 Slow isomer 'H NMR (360 MHz, CDCl₃): δ1.15, 1.35 (t, J=7.5 Hz, 3H each, —CH₂CH₃); 1.87 (s, 3H, OCCH₃); 2.2 (s, 3H, CH₃); 2.87 (d, J=2 Hz, 1H, CHCO₂); 3.85–4.1 (m, 4H, —CH₂CH₃); 4.37 (d, J=2 Hz, 1H, ArCH); 4.75 (bs, 1H, NH); 7.5 (d, J=8 Hz, 1H, ArH); 7.65 (d, J=2 Hz, 1H, ArH); 7.73 (dd, J=2.0, 8.0 Hz, 1H, ArH). m.p. broad, clear melt at 115° C.

EXAMPLE 13

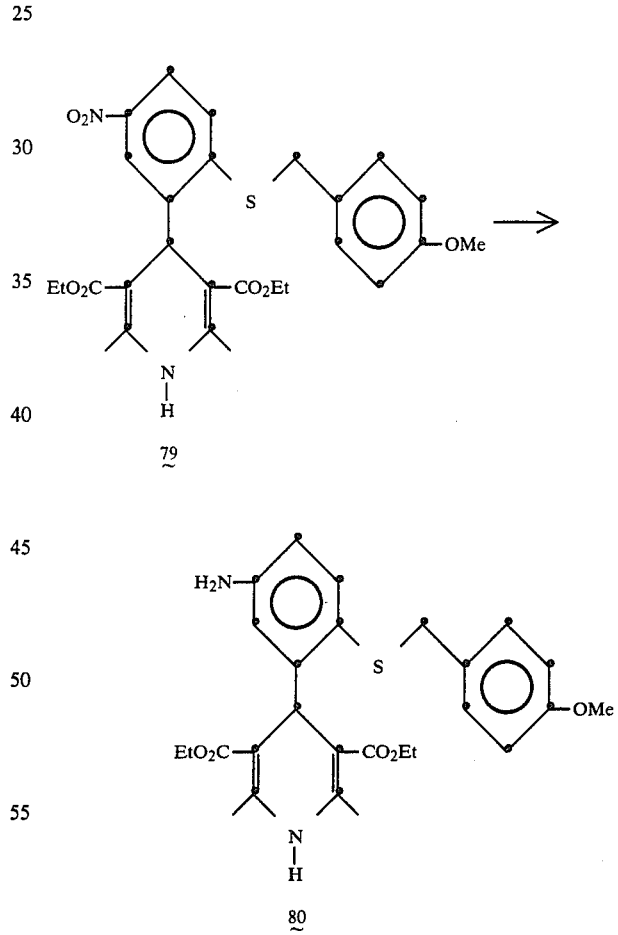

0.526 Grams of dihydropyridine 79 in 3 mL of anhydrous tetrahydrofuran can be treated with 150 mg of lithium aluminum hydride at 0° C. This can then be warmed to 25° C. and the amine isolated in the usual manner to give 300 mg of 80.

EXAMPLE 14

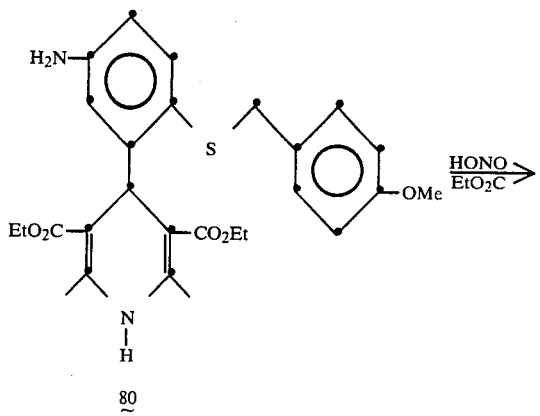

0.500 Grams of amine 80 can be treated using the general procedure with nitrous acid to generate the diazonium salt 81 and this salt can be used for further transformation.

EXAMPLE 15

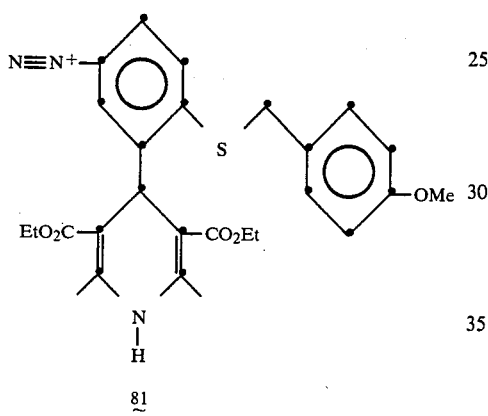

-continued

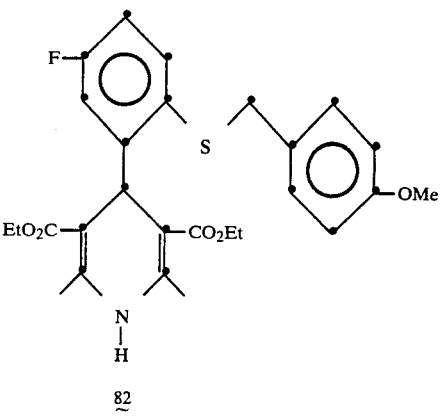

0.40 Grams of diazonium salt 81 can be treated with 0.33 g of tetrafluoroboric acid diethyl ether complex and the precipitate collected and heated to give, after the usual isolation, fluorodihydropyridine 82 (0.15 g).

EXAMPLE 16

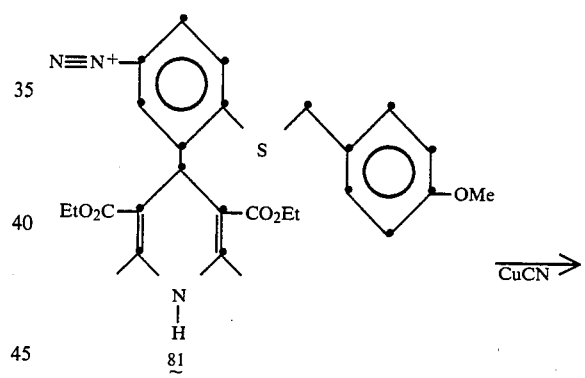

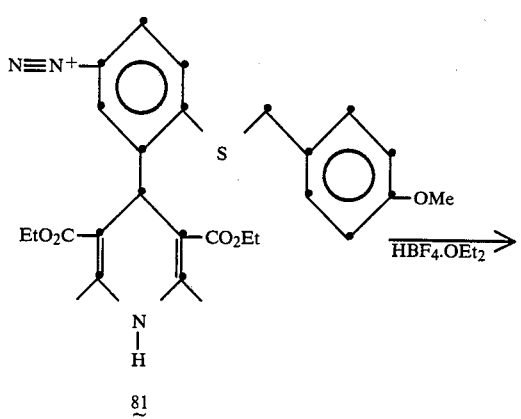

0.30 Grams of diazonium salt 81 can be treated with 0.50 g of copper (I) cyanide to give, after the usual workup, nitrile 83 (0.20 g).

EXAMPLE 17

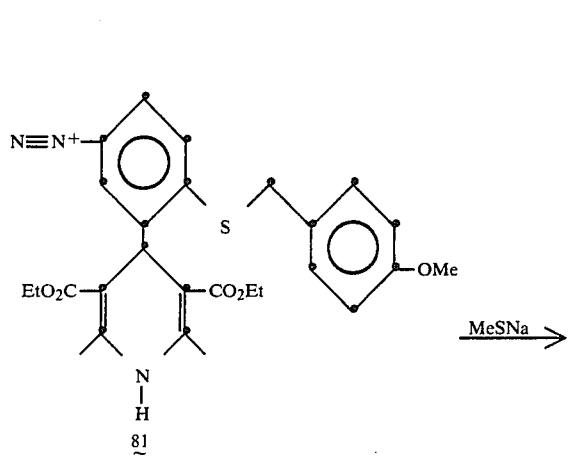

0.30 Grams of diazonium salt 81 can be treated with sodium methylmercaptide (0.2 g) which, when treated under usual conditions, will yield the methylthio dihydropyridine 84 (0.10 g).

EXAMPLE 18

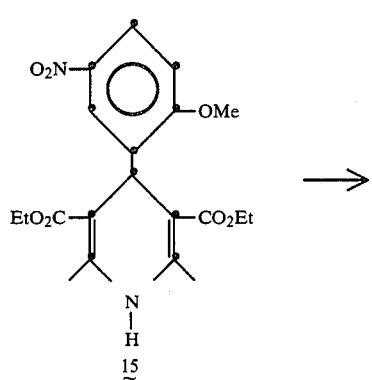

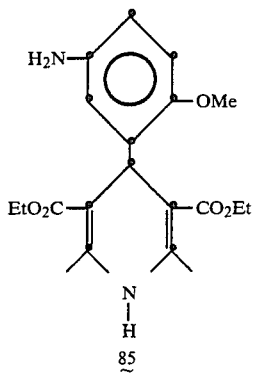

1.00 Gram of compound 15 (Example 1) can be treated with 5% Pd on charcoal under an atmosphere of hydrogen in ethanol to produce dihydropyridine 85 (0.90 g) which can be isolated in the usual manner.

EXAMPLE 19

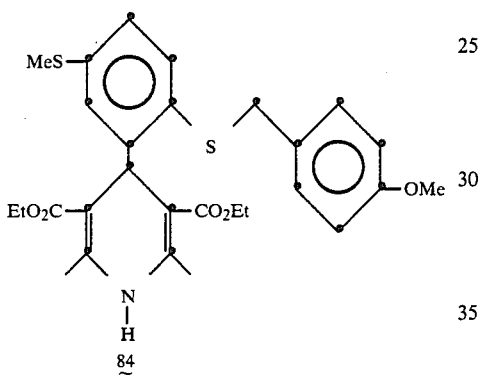

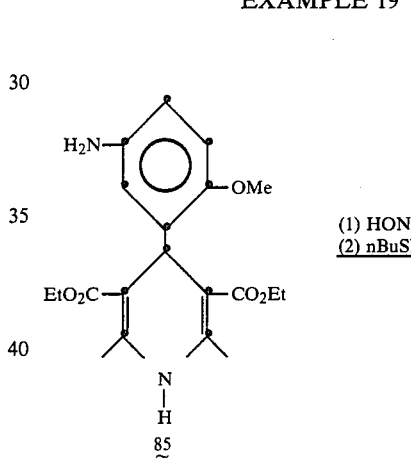

Dihydropyridine 85 (0.50 g) can be diazotized in a manner similar to 17 (Example 1) to give the diazonium species which can then be treated with sodium n-butyl-mercaptide to give dihydropyridine 86.

EXAMPLE 20

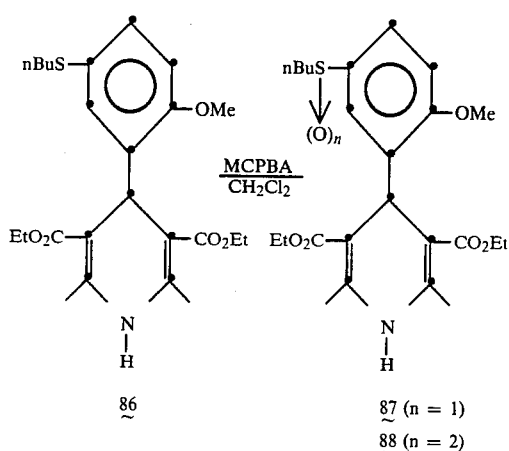

Dihydropyridine 86 can be oxidized with meta-chloroperbenzoic acid in CH$_2$Cl$_2$ to give mixtures of sulfoxide 87 and sulfone 88. Compounds 87 and 88 can then be separated from each other by chromatography on silica gel.

EXAMPLE 21

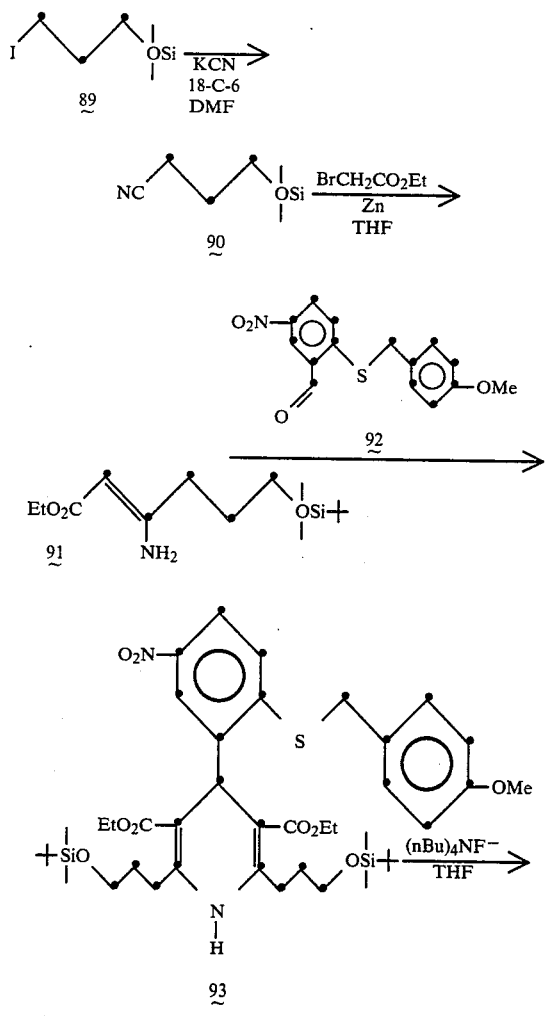

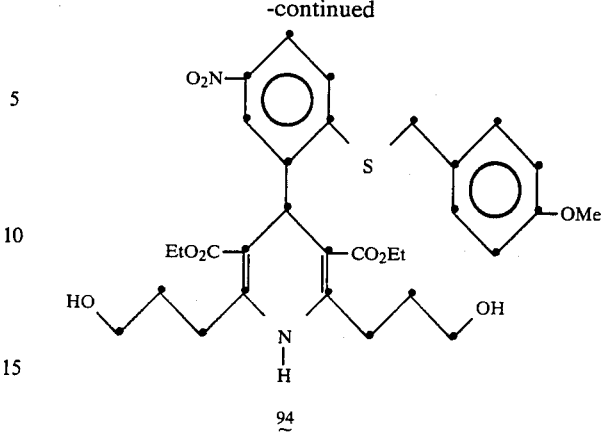

The known iodide 89 (10.0 g) can be treated with 10 g of potassium cyanide in 100 mL of DMF followed by 0.87 g of 18-crown-6 for 20 hours and extracted into ether. After usual isolation procedures, the nitrile 90 can be isolated (6.0 g). Nitrile 90 (6.0 g) can be treated with 9.40 g of zinc dust and 12.6 mL of ethyl bromo acetate in 130 mL of tetrahydrofuran for one hour at reflux to give, after usual workup, amino-crotonate 91 (8.00 g). Compound 91 (8.0 g) can be refluxed with 4.40 g of 92 in isopropyl alcohol for 12 hours to give dihydropyridine 93 (3.80 g).

Dihydropyridine 93 (3.0 g) can be treated with 10 mL of 1.0 molar (nBu)$_4$NF in tetrahydrofuran at 25° C. for 1.5 hours to give, after isolation, diol 94.

EXAMPLE 22

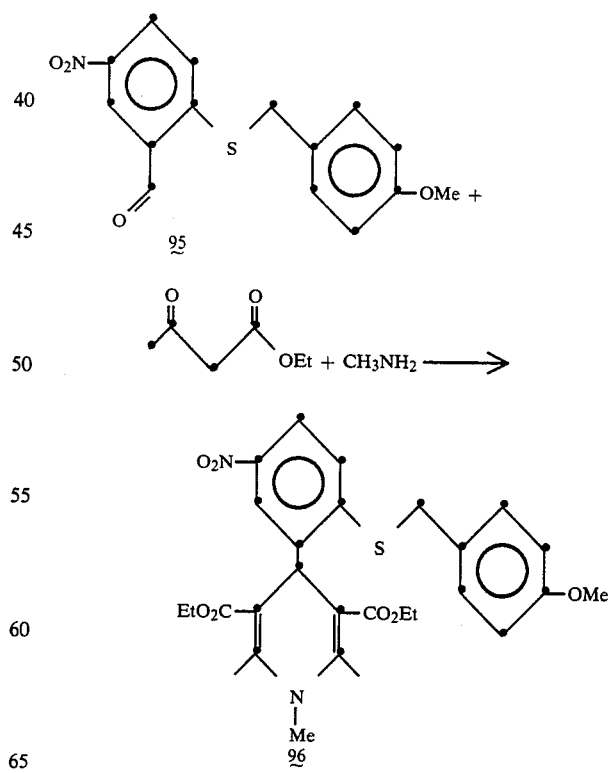

Aldehyde 95 (3.0 g), 3.0 g of ethyl acetate, and 10 mL of 40% methylamine in H$_2$O can be refluxed in 10 mL of isopropanol for 12 hours. After usual isolation procedure, dihydropyridine 96 can be obtained (1.50 g).
EXAMPLE 23
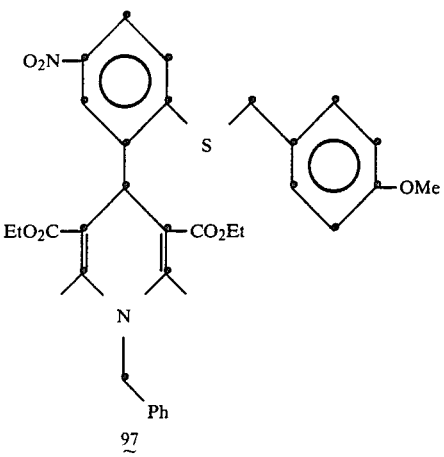
97
Following the procedure of Example 22, benzyl amine can be used to obtain N-benzyldihydropyridine 97.
EXAMPLE 24
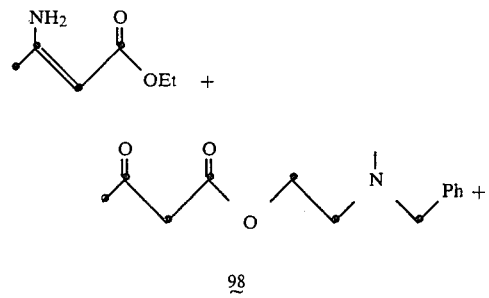
98
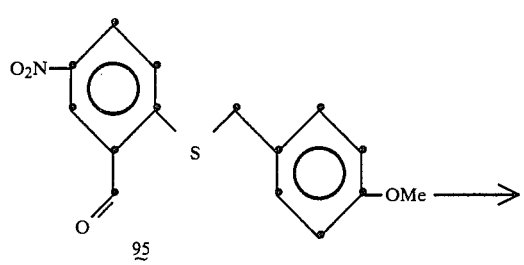
95
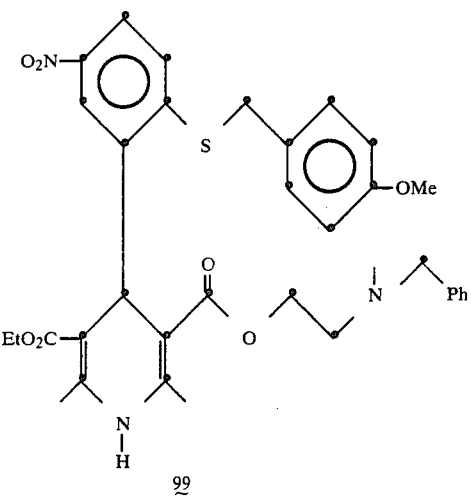
99
Dihydropyridine 99 can be prepared from the acetoacetate 98 using conditions outlined in the literature (*Chem. Pharm. Bull.* 27 (6) 1426–1440 (1979)).
EXAMPLE 25
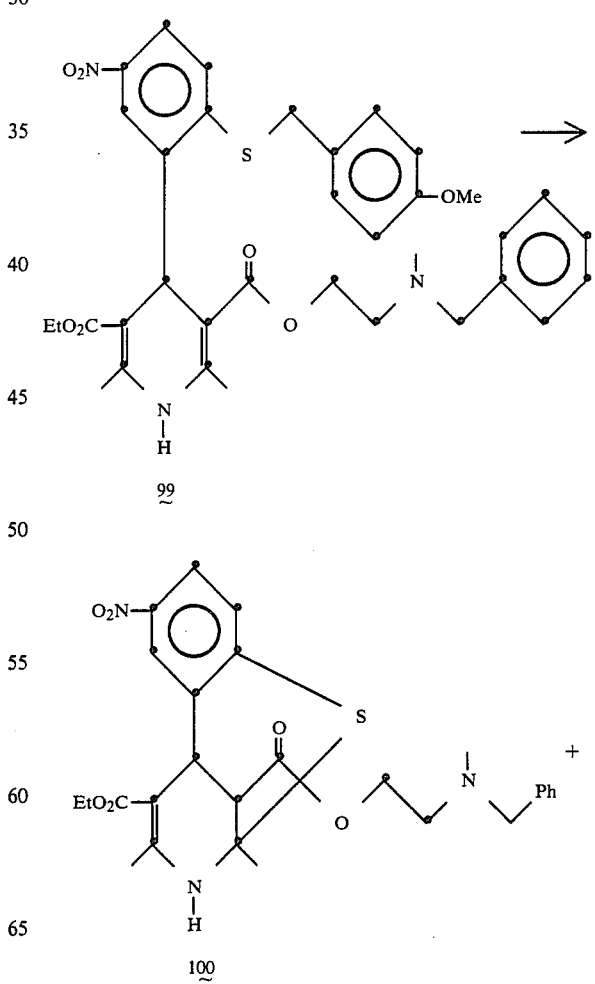
100

-continued

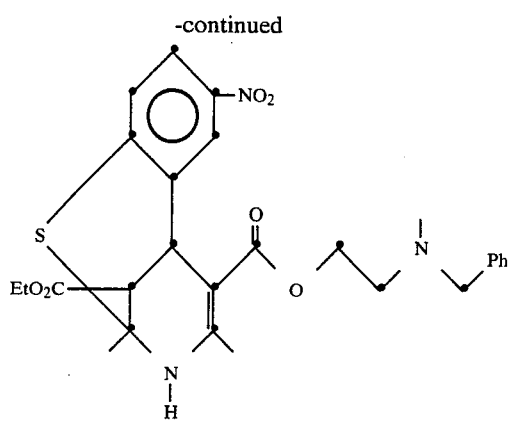

101

Dihydropyridine 99 can be used to prepare both dl pairs of diastereomers 100 and 101 by treatment with trifluoroacetic acid in anisole.

Following the methods shown and described in the Reaction Schemes and using the procedures set forth in the Examples, additional compounds of Formula 1 can be prepared as set forth in Table I below:

TABLE I
Additional Compounds of Formula 1

1

| Compound | X | W | Z | U | n | Y | Method |
|---|---|---|---|---|---|---|---|
| (i) | $CH_3$ | H | H | H | 0 | O | A, B or C |
| (ii) | H | —CN | " | " | " | S | F |
| (iii) | " | $NH_2$ | " | " | " | " | F |
| (iv) | " | F | " | " | " | " | F |
| (v) | " | $CH_3S$ | " | " | " | " | F |
| (vi) | " | $NH_2$ | " | " | " | O | B |
| (vii) | " | n-butyl-S | " | " | " | " | C |
| (viii) | " | $\underset{\text{n-butyl-S}}{\overset{\overset{\text{O}}{\|}}{}}$ | " | " | " | " | C |
| (ix) | " | n-butyl$SO_2$ | " | " | " | " | C |
| (x) | " | $NO_2$ | " | " | " | S | F |
| (xi) | " | " | " | " | " | " | F |
| (xii) | " | " | " | " | " | " | F |
| (xiii) | benzyl | " | " | " | " | " | F |
| (xiv) | H | H | " | " | " | O | C |
| (xv) | " | " | " | $CH_2C\equiv CCH_3$ | " | " | C |
| (xvi) | $CH_3$ | " | " | $CH_2=CHCH_2$ | " | " | A |
| (xvii) | H | $\underset{\text{$CH_3CNH$}}{\overset{\overset{\text{O}}{\|}}{}}$ | " | H | 1 | S | F |
| (xviii) | " | $NO_2$ | " | " | 0 | " | F |
| (xix) | " | " | " | " | " | " | F |
| (xx) | " | " | " | " | 1 | " | F |
| (xxi) | " | " | " | $NO_2$ | 0 | " | F |
| (xxii) | " | H | " | " | 1 | " | F |
| (xxiii) | " | " | $NO_2$ | H | 0 | " | F |
| (xxiv) | " | " | " | " | " | O | A, C or D |
| (xxv) | " | " | H | Ph | " | S | F |
| (xxvi) | " | " | " | $NO_2$ | " | " | F |
| (xxvii) | " | $NO_2$ | " | H | " | O | A, C or D |
| (xxviii) | " | " | " | " | " | S | F |
| (xxix) | " | " | " | " | " | " | F |
| (xxx) | " | " | " | " | " | " | F |

| Compound | R | $R^1$ | $R_4$ | $R^2$ | $R^3$ |
|---|---|---|---|---|---|
| (i) | H | ethyl | ethyl | isopropyl | isopropyl |
| (ii) | " | $CH_3$ | $CH_3$ | ethyl | ethyl |
| (iii) | " | " | " | " | " |

TABLE I-continued

Additional Compounds of Formula 1

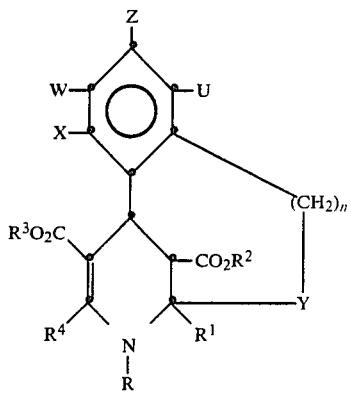

| | | | | | |
|---|---|---|---|---|---|
| (iv) | " | " | " | " | " |
| (v) | " | " | " | " | " |
| (vi) | " | " | " | " | " |
| (vii) | " | " | " | " | " |
| (viii) | " | " | " | " | " |
| (ix) | " | " | " | " | " |
| (x) | " | HO(CH$_2$)$_3$ | HO(CH$_2$)$_3$ | " | " |
| (xi) | " | " | CH$_3$ | " | " |
| (xii) | " | CH$_3$ | HO(CH$_2$)$_3$ | " | " |
| (xiii) | " | " | CH$_3$ | " | " |
| (xiv) | " | " | " | CH$_3$<br>\|<br>PhCH$_2$N(CH$_2$)$_2$ | CH3 |
| (xv) | " | " | " | CH$_3$ | CH$_3$<br>\|<br>PhCH$_2$N(CH$_2$)$_2$ |
| (xvi) | " | ethyl | ethyl | " | CH$_3$ |
| (xvii) | " | " | CH$_3$ | ethyl | ethyl |
| (xviii) | " | " | " | cyclohexyl | " |
| (xix) | " | " | " | ethyl | cyclohexyl |
| (xx) | " | isopropyl | isopropyl | " | ethyl |
| (xxi) | " | ethyl | cyclohexyl | " | " |
| (xxii) | " | CH$_3$ | CH$_2$—cyclohexyl | CH$_3$ | CH$_3$ |
| (xxiii) | benzyl | " | CH$_3$ | " | " |
| (xxiv) | CH$_3$ | " | " | ethyl | ethyl |
| (xxv) | isopropyl | " | " | " | " |
| (xxvi) | H | ethyl | ethyl | cyclopropyl | CH$_3$ |
| (xxvii) | " | CH$_3$ | CH$_3$ | CH$_3$ | cyclopropyl |
| (xxviii) | " | " | " | C$_3$H$_7$O(CH$_2$)$_2$ | C$_3$H$_7$O(CH$_2$)$_2$ |
| (xxix) | " | " | " | CH$_3$O(CH$_2$)O(CH$_2$)$_2$ | CH$_3$O(CH$_2$)$_2$O(CH$_2$)$_2$ |
| (xxx) | " | " | " | (CH$_2$)$_2$—N⟨thiazole⟩S | (CH$_2$)$_2$—N⟨thiazole⟩S |

What is claimed is:
1. A compound having the formula

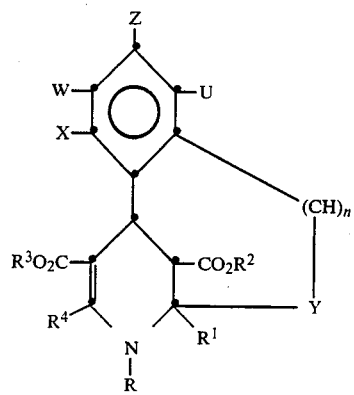

wherein:

R is hydrogen; $C_1$–$C_8$ straight chain or branched alkyl; benzyl;

$R^1$ and $R^4$ are independently hydrogen; straight chain or branched, saturated or insaturated hydrocarbon having up to 8 carbon atoms; hydroxy-$C_1$–$C_8$-alkyl; $C_3$–$C_8$ cycloalkyl; $CO_2$-loweralkyl of $C_1$–$C_8$ $R^2$ and $R^3$ are independently straight chain or branched, saturated or unsaturated hydrocarbon having up to 8 carbon atoms; $C_3$–$C_8$ cycloalkyl;

X, W, Z and U can independently be: hydrogen; phenyl and substituted phenyl wherein the substituents can be 1–2 halo atoms; halo; $NO_2$; trifluoromethyl; $C_1$–$C_8$ alkoxy; $C_1$–$C_8$ linear or branched alkyl, alkenyl or alkynyl; $C_1$–$C_8$ thioalkyl wherein the S atom can be substituted with 1–2 O atoms; cyano; $NH_2$;

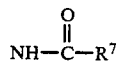

wherein $R^7$ is $C_1$–$C_8$ alkoxy or $C_1$–$C_8$ alkyl; provided that two of X, W, Z and U are hydrogen;

Y is O; S; SO;

n is 0 or 1; and, the pharmaceutically acceptable acid addition salts thereof.

2. The compound of claim 1 wherein:

R is hydrogen;

$R^1$ and $R^4$ are methyl $R^2$ and $R^3$ are $C_1$–$C_4$ alkyl;

X is hydrogen or halo;

U and W can each be $NO_2$; $CF_3$; or halo;

Z is hydrogen;

Y is S; and, n is 0 or 1.

3. The compound of claim 1 having the formula:

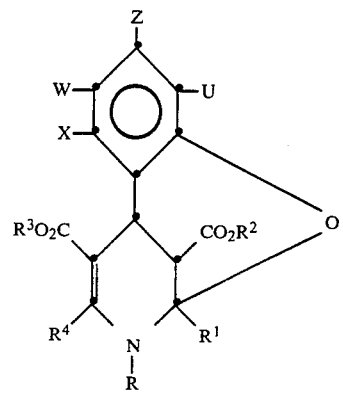

wherein R—$R^4$, W, X, Z and U are as defined in claim 1 and the pharmaceutically acceptable acid addition salts thereof.

4. The compound of claim 1 having the formula:

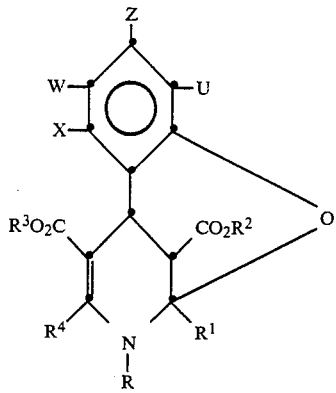

wherein R—$R^4$, X, W, Z and U are as defined in claim 1 and the pharmaceutically acceptable acid addition salts thereof.

5. The compound of claim 1 having the formula:

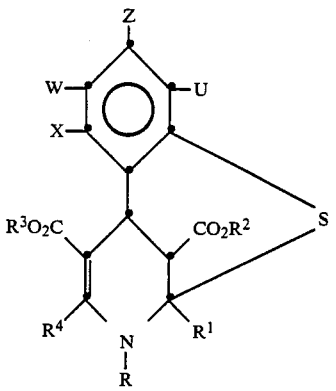

wherein R—$R^4$, X, W, Z and U are as defined in claim 1 and the pharmaceutically acceptable acid addition salts thereof.

6. The compound of claim 1 having the formula:

7. The compound of claim 1 having the formula:

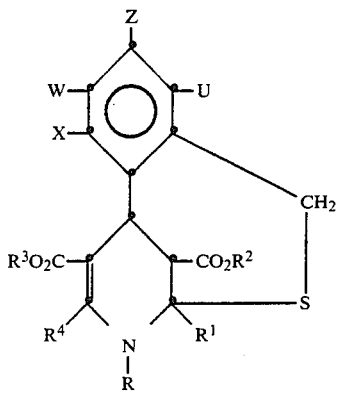

wherein R—R⁴, X, W, Z and U are as defined in claim 1 and the pharmaceutically acceptable acid addition salts thereof.

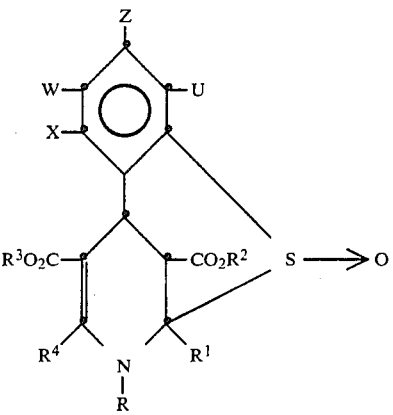

wherein R—$R^4$, X, W, Z and U are as defined in claim 1 and the pharmaceutically acceptable acid addition salts thereof.

8. A compound of claim 1 which is a member selected from the group:
diethyl 3,6-dihydro-2,4-dimethyl-8-nitro-2,6-methano-2H-1,3-benzoxazocine-5,11-dicarboxylate;
diethyl 3,6-dihydro-2,4-dimethyl-2,6-methano-2H-1,3-benzothiazocine-5,11-dicarboxylate;
diethyl 1,3,4,7-tetrahydro-3,5-dimethyl-3,7-methano-2,4-benzothiazonine-6,12-dicarboxylate;
diethyl 1,3,4,7-tetrahydro-3,5-dimethyl-8-(trifluoromethyl)-3,7-methano-2,4-benzothiazocine-6,12-dicarboxylate; and,
diethyl 1,3,4,7-tetrahydro-3,5-dimethyl-8-nitro-3,7-methano-2,4-benzothiazocine-6,12-dicarboxylate.

9. A pharmaceutical composition useful in the treatment of hypertension and arrhythmia, consisting essentially of a pharmaceutically acceptable carrier and a pharmaceutically effective amount of a compound of claim 1.

10. A method for treating hypertension and arrhythmia, comprising administering to a patient in need of such treatment a pharmaceutically effective amount of a compound of claim 1.

* * * * *